United States Patent
Shukla

(10) Patent No.: US 11,058,887 B2
(45) Date of Patent: Jul. 13, 2021

(54) DEVICES, SYSTEMS, AND METHODS FOR NON-INVASIVE CHRONIC PAIN THERAPY

(71) Applicant: NeuraLace Medical, Inc., San Diego, CA (US)

(72) Inventor: Shiv Shukla, San Diego, CA (US)

(73) Assignee: NeuraLace Medical, Inc., San Diego, CA (US)

( * ) Notice: Subject to any disclaimer, the term of this patent is extended or adjusted under 35 U.S.C. 154(b) by 160 days.

(21) Appl. No.: 16/231,249

(22) Filed: Dec. 21, 2018

(65) Prior Publication Data

US 2019/0192874 A1 Jun. 27, 2019

Related U.S. Application Data

(60) Provisional application No. 62/609,330, filed on Dec. 21, 2017.

(51) Int. Cl.
| | |
|---|---|
| *A61N 2/00* | (2006.01) |
| *A61N 2/02* | (2006.01) |
| *A61B 34/20* | (2016.01) |
| *A61B 34/00* | (2016.01) |
| *A61B 34/32* | (2016.01) |
| *A61B 90/30* | (2016.01) |
| *A61B 90/00* | (2016.01) |

(52) U.S. Cl.
CPC ............. *A61N 2/008* (2013.01); *A61B 34/20* (2016.02); *A61B 34/25* (2016.02); *A61B 34/32* (2016.02); *A61N 2/02* (2013.01); *A61B 2034/2048* (2016.02); *A61B 2034/2055* (2016.02); *A61B 2034/2057* (2016.02); *A61B 2034/254* (2016.02); *A61B 2034/256* (2016.02); *A61B 2034/258* (2016.02); *A61B 2090/064* (2016.02); *A61B 2090/066* (2016.02); *A61B 2090/309* (2016.02); *A61B 2090/371* (2016.02); *A61B 2090/395* (2016.02); *A61B 2090/3941* (2016.02)

(58) Field of Classification Search
CPC .......... A61N 2/00; A61N 2/002; A61N 2/004; A61N 2/006; A61N 2/008; A61N 2/02
See application file for complete search history.

(56) References Cited

U.S. PATENT DOCUMENTS

| | | |
|---|---|---|
| 5,263,480 A | 11/1993 | Wernicke et al. |
| 5,299,569 A | 4/1994 | Wernicke et al. |
| 5,470,846 A | 11/1995 | Sandyk |
| 5,540,734 A | 7/1996 | Zabara |
| 6,505,075 B1 | 1/2003 | Weiner |
| 2005/0113630 A1 | 5/2005 | Fox et al. |
| 2008/0064950 A1 | 3/2008 | Ruohonen et al. |

(Continued)

OTHER PUBLICATIONS

International Search Report and Written Opinion for International Patent Application No. PCT/US2018/067369 dated Apr. 1, 2019, 12 pages.

*Primary Examiner* — Carrie R Dorna
(74) *Attorney, Agent, or Firm* — James Scott Nolan

(57) ABSTRACT

Presented herein are devices and systems as well as the methods of using the same for the purpose of reducing and/or ameliorating the sensation of pain, specifically, chronic pain. Particularly, in one aspect, the devices, systems, and their methods of use disclosed herein are effective for reducing peripheral nerve pain, such as resulting from traumatic nerve injury and other types of nerve damage.

20 Claims, 14 Drawing Sheets

(56) References Cited

U.S. PATENT DOCUMENTS

| | | | |
|---|---|---|---|
| 2013/0345491 A1 | 12/2013 | Saitoh et al. | |
| 2014/0343351 A1* | 11/2014 | Tojo | A61N 2/02 |
| | | | 600/14 |
| 2016/0015995 A1 | 1/2016 | Leung et al. | |
| 2017/0296838 A1 | 10/2017 | Asahina et al. | |
| 2018/0071545 A1* | 3/2018 | Saitoh | A61N 2/02 |

* cited by examiner

First pass target area search

Best treatment site selection

Second pass target area search

Setpoints

Tracking region

Maximum distance [ 50 ] mm

Coil to target distance

C2TD [ 2 ] mm

Grid Sizing

1st pass [ 3 ] mm

2nd pass [ 1 ] mm

Colibration treatment time

CTT [ 10 ] s

FIG. 6C

Begin Tracking: Misaligned

Begin Tracking – Misaligned

Tracking : Accurately

Tracking – Aligned/Accurate

DEVICES, SYSTEMS, AND METHODS FOR NON-INVASIVE CHRONIC PAIN THERAPY

CROSS REFERENCE TO RELATED APPLICATION

The present application claims the benefit of U.S. Provisional Patent Application No. 62/609,330, filed Dec. 21, 2017 entitled "Systems and Methods for Non-Invasive Chronic Pain Therapy", the disclosure of which is incorporated herein by reference in its entirety

FIELD OF THE DISCLOSURE

The present disclosure relates generally to the treatment, alleviation, and management of pain. Devices and systems as well as their methods of use are disclosed herein for the treatment, alleviation, and management of chronic pain in a manner that is less invasive, more effective for pain amelioration, and safer to use than traditional methods of pain relief. Particularly, the present disclosure is directed to providing non-invasive therapy for chronic pain.

BACKGROUND OF THE DISCLOSURE

There are many different manifestations of pain. Pain can be psychological, such as caused by depression and stress, or bodily, such as due to a physical perturbation of a part of the body. In particular instances, bodily pain may be caused by direct engagement of the body with physical objects in the world. These types of acute pain are well known, and have been widely treated. Specifically, bodily pain is most often treated by the administration of an analgesic, such as acetaminophen. Additionally, non-steroidal anti-inflammatory drugs, like aspirin or ibuprofen, may be used to alleviate the sensation of pain and/or reduce inflammation.

However, in various instances, such as in extreme pain during post-surgery recovery, non-opioid analgesics may not be sufficient to bring about an alleviation in the experience of pain. In such an instance, opioid-based drugs like codeine or morphine and the like, may be administered. Nonetheless, because of the highly addictive nature of these drugs their use is highly regulated. Despite these ever increasing limiting regulations, opioid abuse remains a national epidemic that continues to claim the lives of tens of thousands of people every year. Particularly, it is estimated that in 2017 opioid abuse claimed the lives of about 72,000 sufferers nation wide.

Thus, when experiencing acute pain, a sufferer has very limited options for pain remediation. They can use an analgesic, such as acetaminophen or an NSAID, which may not be strong enough to relieve acute pain, or they may use an opioid, and risk the possibility of becoming addicted. In either instance, neither medicament is a good option when faced with chronic pain.

It has been found that chronic pain is physiologically different from acute pain. Specifically, acute pain is typically of sudden onset, usually the result of clearly defined underlying causes, such as bodily injury. Hence, healing the underlying cause typically resolves the pain altogether. In such instances, analgesics are administered as a stopgap for ameliorating the sensation of pain until the underlying injury can be healed.

Chronic pain, on the other hand, is different from acute pain. In certain instances, chronic pain can be provoked by an injury that causes inflammation whereby cells at the site of the injury release a variety of biochemical mediators such as prostaglandins, cytokines, e.g., TNFα, IL-1β, IL-6; chemokines, e.g., CCL2, CXCL1, CXCL5; growth factors, e.g., NGF, BDNF; and neuropeptides, such as substance P and CGRP. The release of these injury release factors mediate a cascade of physiological responses that evoke a pathway of pain that persist over time thereby becoming chronic.

Particularly, in particular instances, the injury is to nerve cells thereby initiating a pain pathway that often times generate pain signals that travel from the peripheral to the central nervous system. These pain signals are not easily resolved by the administration of typical pain medicines. More particularly, in either instance, once released, these pain mediators bind to and activate peripheral sensory nerves, which nerves then transmit pain messages to the Central Nervous System (CNS). When pain is acute, this signaling pathway is either not initiated, in the same manner or to the same extent, and/or is relatively easily resolved, as discussed above. However, when such pain is not easily resolved, e.g., due to the release of adverse biochemical mediators, it becomes chronic, which in turn may result in biochemical changes that affect long term alterations in the nervous system, and thereby cause a persistent increase in the number and intensity of pain signal transmission, e.g., peripheral and/or central sensitization.

Accordingly, injuries that adversely affect the peripheral nervous system, such as peripheral nerve injury, often results in the development of chronic intractable pain. As indicated, those suffering from such chronic pain often prove unresponsive to typical, conservative pain management techniques. In such instances, Peripheral Nerve Stimulation (PNS) has been proposed for therapeutic resolution of pain. For instance, Melzack-Wall have proposed a gate control theory of pain that evidences a modicum of pain relief, but is limited to those situations where the pain is the result of injury to the PNS, and the specific nerve being the source of the pain is clearly known and distinguishable. It was neither useful for pain of unknown origins, nor for targeted administration of treatments. Likewise, Sweet and Wespic used electrical stimulation of peripheral nerves in the 1960s, which resulted in a masking of pain sensations with a perception of tingling (paresthesia) that was caused by the electrical stimulation. However, electrical stimulation of nerves in and of itself can be painful, especially with respect to the stimulation of A-β nerve fibers. Subsequent refinements in the technology, surgical techniques, and patient selection have led to some improved long-term results, but these procedures are invasive and/or are not generally applicable.

In addition to the use of electrical stimulation for the treatment of the sensation of bodily pain, the use of electrical stimulation for the treatment of emotional pain, attendant to psychiatric disorders, has also been proposed. Particularly, efforts have been made to treat psychiatric disorders with peripheral/cranial nerve stimulation. For instance, U.S. Pat. No. 5,299,569 discloses that some partial benefits have been experienced with respect to pain relief by electrically stimulating the vagus nerve. U.S. Pat. No. 5,470,846, discloses another example of treating emotional pain by electrical stimulation, in this instance depression, by the use of transcranial pulsing of a magnetic field. Yet further, U.S. Pat. No. 5,263,480, asserts that stimulation of the vagus nerve may be beneficial for the treatment of depression and compulsive eating disorders. Furthermore, U.S. Pat. No. 5,540,734 discloses the stimulation of the trigeminal and glossopharyngeal nerves for the treatment of depression as well as other various psychiatric illnesses. Further still, U.S.

Pat. No. 6,505,075 discloses peripheral nerve stimulations of the C2 dermatome area of the eye so as to treat intractable headaches that originate in the back of the head in the C2 dermatome area. This method of delivering electrical stimulation energy to the C2 dermatome area involves positioning stimulation electrodes in the fascia and subcutaneous regions proximate the C2 dermatome. Further research has shown that electrical stimulation may be used for treating neurological diseases, including such disorders as Parkinson's disease, essential tremor, dystonia, and chronic pain.

Accordingly, in view of the above, in very limited circumstances, electrical stimulation may at times be advantageous for treating neuro-related maladies. This is significant because typical methods for treatment of such disorders often involve performing one or more lesions in the neural tissue, which thereby destroys the nervous system tissue in an attempt to modulate neuronal activity. Particularly, for many forms of intractable pain, e.g., occipital pain, traumatic brain injury, etc., which have proven to be resistant to analgesic medications, traditional treatment options typically involve chemical, thermal, or surgical ablation procedures as a way of reducing the sensation of pain. For instance, surgical procedures for treating intractable pain include neurolysis and/or nerve sectioning.

However, in various alternative instances, it has been determined that direct electrical stimulation is useful for modulating target neural structures without resulting in the destruction of nervous tissue. The methods for using such electrical stimulation include electroconvulsive therapy (ECT), transcranial direct current stimulation (tDCS) and vagal nerve stimulation (VNS). Specifically, a procedure for producing indirect brain electrical stimulation can be achieved via transcranial magnetic stimulation. For example, transcranial magnetic stimulation (TMS) provides a non-invasive method for activating the human motor cortex such as for assessing the integrity of the central motor pathways. TMS is based on the principle of electromagnetic inductions. It has been determined that if rapidly changing magnetic pulses are generated and directed toward the skull at an appropriate frequency, the pulses can penetrate the scalp and induce a secondary ionic current in the brain. Depending on the stimulation setting, single stimuli can either excite or inhibit neuronal functions.

Accordingly, in certain limited instances, magnetic stimulation, e.g., dynamic magnetic flux, can provide a non-invasive method for modulating nerve function and has been proposed to be used for chronic pain management. However, aside from stimulating the brain, the use of dynamic magnetic flux in transcutaneous stimulation for pain relief has not been established. This is the result of a number of issues: 1) the current commercially-available magnetic stimulators are physically very bulky; 2) necessary coils usually require additional cooling units to prevent overheating; 3) the devices are too expensive to be accessible to the general public; and 4) operating the device requires special training and clinical expertise. These physical limitations, cost, and the requirement of special training restrict the current scope of use of this non-invasive means of pain management outside of healthcare facilities.

Accordingly, the need remains for a device that is affordable and easy to use that makes tMS an effective tool for management of chronic pain, readily available. The present disclosure is directed to devices, systems, and methods for addressing this unmet need.

SUMMARY OF THE DISCLOSURE

The present devices, systems, and methods accomplishes these goal by providing for noninvasive pain therapy, including (but not necessarily limited to) an automated positioning and tracking system that is programmed and/or configured to selectively position a magnetic coil proximate a target area so as to deliver chronic pain therapy to a predetermined nerve target location in a subject in need of therapy.

For instance, in one aspect, a transcutaneous magnetic stimulation (tMS) device including a magnetic coil is provided, such as where the tMS device is configured as a magnetic stimulator. In various embodiments, the tMS device may be coupled to a positioning element that is configured for assisting in the positioning and/or orientating of the tMS device so as to be proximate the site of treatment. This may be performed manually or autonomously, such as through an associated controlling device.

Accordingly, in another aspect, a system is provided, where the system includes a tMS device, configured for generating and direction a therapeutic magnetic field toward a treatment site, a positioning element, such as a robotic arm, that is configured for orienting and/or positioning the tMS device and/or magnetic coil proximate the treatment, and a control unit, such as a computing device, which is configured for controlling the operations of one or more of the tMS device, with respect to the generation and/or application of the magnetic field, and the positioning element, such as with respect to its movements in three-dimensional space. In various embodiments, a distance determining device and/or imaging component may also be included, where the placement and positioning of the tMS device and/or magnetic coil may be accomplished through the cooperative interaction of one or more of: the positioning element, a stereoscopic camera, a micro laser distance scanner, and proprietary software operating on a computing system in communication with the various components of the system. The devices and systems of the present disclosure will greatly improve application of non-invasive chronic pain relief therapy.

Consequently, in a further aspect, one or methods is herein presented, such as for the therapeutic delivery of a magnetic flux to a site of injury or pain to a subject suffering therefrom. For instance, during therapy, the positioning element, which may include a robotic arm, may be configured to function along with the other system components so as to precisely track and align the magnetic coil of the tMS device at the desired area of treatment. In various instances, in so doing, the system may be configured to capture and/or build one or more three-dimensional measurements and/or representations of the space in which the components of the system are operating within.

Accordingly, a 3-D measurement instrument and/or stereoscopic camera, and/or laser distance sensor may be configured to provide real time position feedback data of the patient/area of treatment, positioning element, and tMS device with coil to the control module. Hence, using this data the position of the positioning element with respect to the tMS device and the target area and/or treatment site may be adjusted to maintain/administer optimal therapy to the patient. The system may also be equipped with safety measures to allow system operation and application of therapy at minimal risk to patient and clinician.

In a particular embodiment, therefore, a system for delivering transcutaneous magnetic stimulation (tMS) to a treatment site on a body of a subject is provided. The system may include a tMS device, a positioning element, an imaging component, a distance scanner, a reflective marking device, and a control module. For instance, the system may include a tMS device such as where the tMS device is configured for delivering a focused magnetic flux to the treatment site when positioned proximate the body of the subject. Particularly, the tMS device may include a housing having an extended body, which includes a proximate portion having a proximate end, and a distal portion having a distal end. In certain instances, the extended body may define a cavity for retaining one or more components of the tMS device. Likewise, the tMS device may include an insulated magnetic coil, such as disposed within the proximate portion of the extended body of the housing, where the magnetic coil is configured for generating and delivering a focused magnetic flux, e.g., at a determined pulse rate. The tMS device may also include a control module that is in communication with the magnetic coil, which control module is configured to control the focused magnetic flux and the pulse rate to be delivered by the magnetic coil of the tMS device so as to deliver a magnetic flux to the treatment site of a subject to be treated.

The system may further include a positioning element, such as having a proximal portion including a proximal end, and a distal portion including a distal end, where the distal portion is coupled to the magnetic coil proximate the distal end. The positioning element may be composed of a plurality of articulating arm members, where the plurality of the arm members are coupled together by an automating element, e.g., a motor, the automating element for assisting in the positioning of the tMS device proximate the treatment site.

An imaging component may also be included such as where the imaging component includes one or more image capturing devices, such as a camera. In various embodiments, each image capturing device may be configured for capturing one or more images defining a three-dimensional space that is occupied by one or more of the subject, the tMS device, and the positioning element. A distance scanner may also be included where the distance scanner is coupled to one or more of the housing of the tMS device and/or to the image capturing device, such as where the distance scanner is configured for determining a distance between the magnetic coil and the treatment site on the body of the subject to be treated.

A reflective marking device may further be including such as for assisting with the positioning of the tMS device. For example, the reflective marking device may be positioned proximate the treatment site. In various instances, the reflective marking device may include a plurality of reflective elements that are configured for reflecting back a light emitted from the distance scanner in a manner sufficient for enabling the distance scanner to determine the distance between the magnetic coil and the treatment site.

Additionally, the system may include a control module that may be coupled to the proximal portion of the positioning element near the proximal end, such as where the control module is configured for controlling one or more of the tMS device, the positioning element, the imaging component, and the distance scanner. A further control unit, such as a stand alone desktop or laptop computer may also be provided, such as where the control unit serves as a master control unit for the system and is in communication with one or more of the tMS or positioning element controllers.

Illustrative embodiments of the disclosure are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to an enterprise resource software system or other business software solution or architecture, it should be readily understood that such features are not intended to be limiting. The claims that follow this disclosure are intended to define the scope of the protected subject matter.

BRIEF DESCRIPTION OF THE DRAWINGS

FIG. 6C provides a representation of a GUI displaying a tracking functionality.

DESCRIPTION OF THE DIFFERENT EMBODIMENTS

Figure 1A:
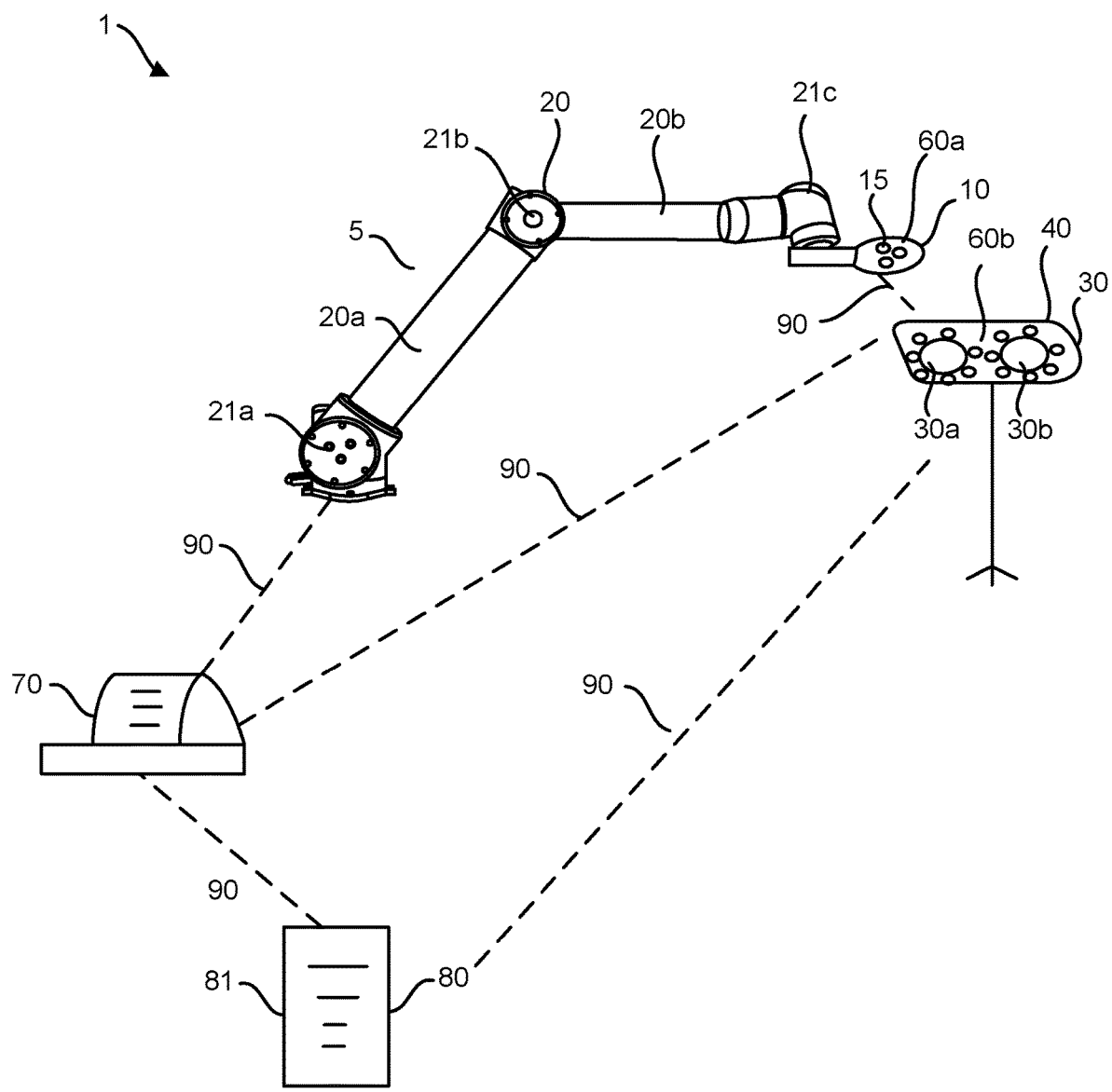
FIG. 1A provides a schematic representation of an embodiment of the system of the disclosure.

Accordingly, the present devices and systems as well as the methods of using the same are provided for the purpose of reducing and/or ameliorating the sensation of pain, specifically, chronic pain. Particularly, in one aspect, the devices, systems, and their methods of use disclosed herein are effective for reducing peripheral nerve pain, such as resulting from traumatic nerve injury and other types of nerve damage. For instance, generally, there are two types of pain that are the result of injury. The first is acute, fast onset, mediated by A-$\delta$ nerve fibers, while the second is a duller, slow pain, mediated by C nerve fibers. For example, when a part of the body is injured, the first pain felt is typically sharp, specific, and acute, while a few seconds later a more diffuse, dull pain is typically experienced.

These two different types of pain sensation are the result of the conductance of pain sensation by different nerve cells. Specifically, there are generally two types of pain fibers, A and C nociceptive nerve fibers, which result in two types of pain sensation: fast and acute as well as a slower more dispersed and duller sensation of pain. Nociceptive nerve fibers have free nerve endings (nociceptors) that form dense networks with multiple branches that connect the peripheral tissues and organs to the spinal cord. These nociceptors respond only when a stimulus is strong enough to threaten the body's integrity, such as when a stimulus or event is likely to cause an injury.

As indicated, these two distinct sensations of pain are distinguishable by the speed at which the different nerve fibers conduct their signaling. For instance, A and C fibers differ in the diameter and thickness of the myelin sheath that surrounds them, which affects the speed at which these neurons conduct nerve impulses. Specifically, the greater the diameter of the fiber and the thicker its myelin sheath, the faster the nerve cells will conduct nerve impulses. More specifically, A fibers have a larger diameter and are myelinated, and therefore conduct impulses quickly, while C fibers have a smaller diameter, are not myelinated, and conduct impulses more slowly. Accordingly, because of their differences in diameters and myelination, these different nerve fibers have been adapted to serve different functions.

For example, A fibers can be divided into three sub-categories including A-$\alpha$ fibers, which carry proprioception, or orientation, information, A-$\beta$, which carries information about touch, and A-$\delta$, which carry information about pain, such as mechanical and/or thermal pain. C fibers also conduct information about mechanical and chemical, e.g., cold-sensation, pain, but with a slower conduction velocity. Accordingly, it is the difference between the speeds at which the two types of nociceptive nerve fibers (A-$\delta$ and C) conduct nerve impulses that distinguishes the two different manners in which pain is experienced when injured, the first, A-$\delta$, is mediated by a fast-pain pathway that causes the immediate sharp, and acute pain, while C fibers form a slow-pain pathway that leads to the sensation of diffuse and dull pain. Likewise, A-$\alpha$ fibers regulate the sensation of pain as related to one's muscles. However, there is another, lesser-known pain pathway that is mediated by an abridgement in homeostasis, which pain pathway is arbitrated by A-$\beta$. This pain pathway is exemplified by arbitrating neuropathic pain.

When in a homeostatic condition, e.g., in the absence of an acute pain causing event, everywhere in the body where pain is not felt, this absence of the sensation of pain is the result of a particular sensory nerve fiber, A-$\beta$, in that region that is constitutively active at a baseline level the functioning of which is to signal to the brain that homeostasis is good and to be maintained. However, when that homeostatic condition is perturbed, pain is perceived when there is trauma or damage to the nerve that results in a diminution of activity below A-$\beta$'s basal level. This decrease in activity signals to the brain that an injury to the body, at site of onset, has occurred and as a result the brain interprets this drop in activity as a traumatic event and therefore signals pain.

Particularly, the mechanism for this cause of action involves messaging from secondary, peripheral nerve fibers to the primary, first-order nerve fibers in the dorsal root ganglia. More particularly, the dorsal root ganglia constitute a cluster of neurons that form at the dorsal root of the spinal nerve. These neurons include a collection of afferent axons that function to relay sensory information, in this instance, a decrease in peripheral sensory activity, e.g., of A-$\beta$, from the periphery to the central nervous system, e.g., brain, via the spinal cord. Specifically, when the peripheral A-$\beta$ sensory touch fibers are active, the dorsal root ganglia (DRG) filters both A-$\delta$ and C fiber activity. However, when A-$\beta$ activity diminishes, the filtering at the DRG switches off, and A-$\delta$ and C fiber signaling is then passed on to the central nervous system. Hence, it has been determined herein, that A-$\beta$ sensory input play a suppressive role for repressing A-$\delta$ and C fiber activity, and when that suppression is lifted, e.g., by a decreased activity of A-$\beta$, acute and/or chronic pain signaling is initiated.

Accordingly, in a normal condition, when a portion of the body suffers an injury, A-$\beta$ activity is down regulated, and A-$\delta$ and/or C fiber activity is increased signaling a pain response. When the body heals, homeostasis is re-established, A-$\beta$ activity is increased, e.g., gradually, and the pain is diminished. However, in some instances, such as when the nerves are traumatically injured, even though the body may heal, the nerves may not. Hence, in such an instance, e.g., of traumatic nerve injury, A-$\beta$ activity remains down regulated, and because of this a chronic sense of pain remains ongoing.

Unfortunately, until the Applicants' work in this field, there has been little advancement towards the healing and/or amelioration of neuropathic chronic pain caused by diminished A-$\beta$ activity. Specifically, as indicated above, analgesics and/or opioids have been proposed for the purposes of diminishing pain perception, however, for the reasons stated above, analgesics are often not sufficient for alleviating pain, e.g., acute pain, and though opioids are often effective for alleviating such pain, they are addictive and have been the cause of death for hundreds of thousands of American's world wide. Additionally, although useful for the amelioration of pain caused by A-$\delta$ and C fiber activity, these medicaments are not particularly useful for reducing the chronic pain that results from a down regulation of A-$\beta$ activity.

However, because of the Applicant's realization of the A-$\beta$ pain pathway and its mechanism of action, as well as subsequent work performed in this field, a device and a method for using the same for ameliorating pain, such as A and C fiber pain, especially A-$\beta$ pain, is hereby proposed.

More specifically, the inventor has determined that by stimulating the A-β nerve at the site of pain, A-β activity can be increased, which in turn down regulates the activity of A-δ and C fiber activity, thereby reducing the experience of pain. Such stimulation is difficult to administer, however, because the A-β nerve fiber mediates touch sensitivity. Particularly, because of this, any direct stimulation of the A-β nerve, e.g., such as through electro-stimulation, will result in direct pain being caused due to hypersensitivity to touch and/or making contact with the site of pain, such as through electrode insertion. This difficulty has been overcome by a number of different advancements in the field made by the inventor hereof.

Particularly, it has been determined that the A-β nerve at the site of pain can be stimulated in a non-invasive manner, such as by electromagnetic stimulation. Likewise, it has further been determined that when such electromagnetic stimulation is administered at a determined frequency, it can result in the activation of the A-β nerve, which, in turn, will result in the interruption of the pain response and a cessation of pain experience. More particularly, magnetic stimulation may be administered at a current density so as to create a voltage differential at the axon of the A-β fiber thereby activating the various voltage gated channels therein, which in turn, results in the activation of A-β and the down regulation of by A-δ and C fiber activity. Accordingly, provided herein is a device for the application of electro-magnetic stimulation of the nerve cells, specifically the nerve cells associated with pain mediation, more specifically, A-β nerve fibers.

It is to be noted that because it has been determined that A-β is a fast conducting nerve fiber, its signaling will reach the DRG prior to that of A-δ and C fiber activity, thus, resulting in a cessation of the experience of pain, so although one or more other nerve fibers may be stimulated, the rapid conductance of the A-β nerve fiber should assure that its activation dominates the interaction in a manner so as to cause a diminution in pain. Such stimulation may be generated in any suitable manner so as to activate the A-β nerve fiber, e.g., above its basal level, so as to increase the signaling that thereby down regulates the sensations of pain caused by the activation of A-δ and C fibers. For instance, such stimulation may be generated by a source of magnetic stimulation or other stimulation that can activate the voltage gated channels in the nerve fiber and/or depolarize the nerve cell, such as in the lease invasive manner.

However, although effective for lessening pain, the activation of A-β nerve fibers with magnetic stimulation is difficult to achieve. Specifically, in order to generate stimulation of the A-β nerve so as to produce activation, the magnetic stimulation needs to be finely tuned, which means that it is very easy to go off of the treatment site. Consequently, to overcome these difficulties, the development and use of the electro-mechanical devices, systems, and their methods of use described herein have been advanced for overcoming these difficulties. Specifically, in various embodiments, a mechanism for orientating a tMS device proximate an active region, e.g., a site of acute and/or chronic pain, such as within a determined range of effective administration of electromagnetic radiation, as well as the methods for delivering such radiation are provided. More specifically, a mechanism for identifying a treatment site and orientating the administration of electromagnetic radiation to a subject are provided, such as where the mechanism includes a positioning element, such as a robotic arm, and the administering element includes a tMS device.

Accordingly, in various embodiments, a robotic arm is provided as a positioning element for orienting an electromagnetic stimulation device, e.g., a tMS device. Specifically, a positioning element, such as a robotic arm, is useful for positioning a discrete magnetic field, such as generated by a tMS device, proximate a treatment site in a manner that is sufficient to align a generated magnetic field in an orientation that is capable of activating a nerve cell, such as an A-β nerve fiber, to thereby ameliorate the experience of pain at the treatment site. Accordingly, in various embodiments, a system for the positioning of a stimulating, e.g., tMS, device is provided where the system functions for the purpose of orienting the tMS device proximate an identified target and/or treatment site. For instance, in various instances, a positioning element, e.g., a robotic arm, is provided so as to align a discrete magnetic field with a fine nerve fiber in a manner such that a generated magnetic field can activate the particular pain causing nerve cell in a manner to raise its activity above a threshold level so as to thereby abate the experience of pain.

As indicated the stimulating device is typically a device for generating and applying a force field so as to stimulate one or more nerve fibers, such as the A-β nerve fibers, so as to increase activity therein above its baseline condition. Particularly, the force field is a magnetic field, generated by a magnetic stimulatory device. Other field generating devices can be used, such as for delivering electromagnetic radiation, light and/or electricity, and in some instances, though not ideal, a physical stimulatory device may be employed, such as including one or more electrodes, or needles, such as for increasing conduction, such as via an acupuncture style needle and/or electrode, such as in addition to an appropriately configured EMG and feedback device. However, these modalities may cause a sensation of heating or burning and/or may cause pain via direct contact with the nerve, which is not ideal, and these modalities are further complicated by the high impedance of the skin. More particularly, with respect to electric stimulation of the A-β nerve fiber, another difficulty is that current flows through the path of least resistance, and thus, applying current and directing it to the identified nerve fiber is difficult to do and maintain, especially, when the subject is hyper sensitive to touch as is the A-β nerve fiber. Likewise, the introduction of new electrons will change the physics and chemistry of the tissue and/or affects the concentration gradient.

Application of a therapeutic treatment in these regards is difficult to do, in part, because it is challenging to identify a specific nerve fiber, e.g., an A-β nerve fiber, amidst all the other cell tissues within a given region of the body, and is further complicated by the difficulty of determining the necessary characteristics of the magnetic field that are sufficient to generate nerve activation within the appropriate parameters. Additional difficulties surround the targeting of the generated magnetic field with the appropriate characteristics in such a manner that the generated field actually arrives at the identified nerve tissue and in the appropriate condition to provoke the desired activation. Further complications include making this targeting and administration consistent over treatment regimes and across a multiplicity of treatment days. More specifically, because the various different nerve tissues are disperse, and the distribution of their nociceptors form dense networks with multiple branches, targeting a particular nerve cell, e.g., an A-β nerve fiber, for receipt of the fine tuned magnetic stimulation is problematic.

A systematic method, therefore, for targeting and treating a site of chronic pain is hereby provided. In various embodiments, this method may include one or more of the following steps: Defining a target area of a subject's body in need of treatment; Positioning a magnetic stimulation device proximate the defined target and/or treatment area; Determining one or more characteristics of a magnetic wave to be delivered to the target area; Administering the determined magnetic stimulation to the treatment site, e.g., in a manner to provoke bi-lateral stimulation in a nerve cell, e.g., an A-β nerve fiber; Eliciting feed-back from the subject so as to evaluate the effectiveness of the targeting; and then optimizing for depolarizations of the targeted sensory nerve fiber, such as by varying the amplitude of the waveform.

There are several ways by which these objectives may be achieved. For instance, a grid-like structure may be applied to the treatment region whereby the treatment region can be broken down into sub-regions and through an iterative process of application of magnetic stimulation a narrowly defined active site can be identified. For example, a grid of rows and columns forming boxes can be applied to the treatment region. In particular embodiments the grid can be formed from 3 to 6 to 9 to 12 to 16 boxes that together form a larger box that defines the boundaries of the target region. The boxes can vary in size, such as where each box may be from about 3×3 mm to about 9×9 mm to about 12×12 mm in area, depending on the target are and/or treatment site, e.g., whether it's smaller than a finger or larger than hand, etc. Regardless of size, stimulation can be delivered iteratively to the various sub-regions of the target region until all areas proximate the treatment site have been suitably identified.

Specifically, when a magnetic pulse is delivered to the appropriate pain signaling nerve fiber, in the correct orientation, so as to stimulate activity in the nerve cell, a concomitant dulling of the pain will be experienced by the subject, and the box defining that targeted site can then be identified as part of the treatment area. This process can be repeated until an adequate number of areas have been identified so as to define the treatment site such that by applying one or more magnetic pulses to the treatment site results in the diminution and/or total abeyance of pain sensation. For instance, in various embodiments, the grid may be laid out like a telephone key pad with numbers from 1 to 9, stimulation is provided to each number, e.g., sequentially, and for each number the subject can self-report an evaluation on the pain diminishment, such as using a scale from 1 to 10, and in this manner each box particularly defining the precise bounds of the treatment site may be defined.

Particularly, by aligning the active boxes, the topographical distribution of the nerve may be defined such as by horizontally, vertically, or diagonally aligning the active boxes, e.g., where three sequential numbers demarcate a horizontal distribution pattern, any number separated by three demarcate a vertical distribution pattern, and a sequence of odd numbers demarcates a diagonal distribution pattern. Of course, other patterns can also be identified based on the characteristics of the nerve distribution.

Accordingly, in a manner such as this the nerve to be treated may be clearly identified, localized, and treated, as discussed herein, resulting in a decrease of pain sensation. In certain embodiments, once the treatment site has been localized, it may further be defined into smaller units, so as to further refine the locus of pain origination. Additionally, depth may be accounted for by varying the amplitude and/or distance of the stimulation device from the site of treatment.

Further, in various instances, the dimensionality of the treatment site may be catalogued in such a manner that treatment can be delivered to the same position in the same orientation so as to make the administration of the magnetic field uniform. In this manner, the use of an automated delivery vehicle, such as a robotic arm, for the positioning of the source of magnetic energy application, e.g., the tMS device, is especially useful because it allows for a degree of certainty, e.g., sub-millimeter accuracy, in the positioning and orientation of the application device with a rapidity above that which can be achieved without such use.

For instance, it is extremely difficult, if not impossible, to position the magnetic stimulation device in the same position for any two given treatment sessions, if it is positioned by human hand. Particularly, when positioning the stimulation device by hand, fine motor movements are required beyond that which is humanly feasible, and thus, both under- and overcompensation often results. More particularly, it is practically impossible to achieve a repeat in locality of application because human motor skill development does not provide for millimeter and sub-millimeter accuracy in positioning, with respect to repeatability and accuracy.

Another advantage of an electronic positioning element, such as a robotic arm, is motion compensation. Specifically, motion compensation is difficult to achieve and maintain in a non-animated format. Particularly, it is difficult to effectuate localization in a reproducible manner. Often performing this task manually is time consuming and can result in causing pain to the subject to whom the treatments are being administered. For instance, manual localization can roughly be achieved in from about 15 to about 20 or 30 minutes, and is not readily reproducible across treatments, while using an automated system, as disclosed herein, this time can be reduced to under 5 minuets, such as under 3 minutes, particularly under 1 minute and 30 seconds, such as under 60 or 45 or 30 seconds or less, without causing substantial pain to the subject. This localization task is made more difficult because the nerve fiber to be treated is a very fine nerve, and during attempted administration, the subject has a tendency to move, if ever so slightly, which can then go off the treatment site. Particularly, where the nerve to be treated is sub-millimeters in length, a small adjustment of the subject can result in a wide miss of the treatment site, with little fine-movement of manual manipulation of the application instrument.

The present system, however, is configured for performing fine-tuned target locking and movement compensation, which allows for increased focusing on the optimal target site. More particularly, results have shown that even though manual targeting is useful, such as with a 30% efficacy, when using the present system efficacy can be increased by about 5% or 6% to about 10% or about 20%, and in some instances, an increase of about 30% to about 40% or about 50% or more, which can be accretive over time with additional sequential treatments. Hence, even at the low end, after three treatments, by the third treatment the subject can experience about a 60% to about a 70% or 75% or even up to about 80% or 85% reduction in pain, and in some instances, about 90% or 95% or more.

Thus, the use of the present positioning system not only solves for the problem of position error, such as by targeted application, but also result in an increase in effectiveness and/or efficacy in treatments overall. For instance, it has been observed that after a plurality of treatments, such as 2, 3, 5, or 6 or more, the length of time between treatments may be extended for longer and longer periods of time, such as due to increased periods of the absence of pain. In one example, after 3 treatments in the first week, a whole month of pain relief may be observed. Hence, after one-month, the subject may only need treatment once a month for an entire month of pain relief.

Additionally, in various embodiments, a visioning module such as including an imaging device, such as a 3-D scanner, can be used to scan and image the treatment site so as to generate a three-dimensional representation of the treatment site, which further increases both targeting and effectiveness and further increases repeatability. For instance, the imaging device may include a lighting element and an imaging capturing device. Specifically, the lighting element may be capable of generating ultraviolet, visible, or infra-red electromagnetic radiation. For instance, the lighting element may include a series of lighting elements that are positioned proximate one or more of the lenses of the image capturing component. Particularly, a plurality of lighting elements are configured so as to circumscribe a circumference of the image capturing component itself or one or more lenses thereof. For example, a collection of lighting elements may be positioned around each lens of a camera element, such as a stereoscopic camera element. In particular instances, the lighting elements may include or otherwise may be replaced by one or more sensors, such as a distance measuring sensor. In certain instances, the lighting element is a semiconducting electrode, such as a concentrated light emitting diode, LED, and the image capturing device may be configured for capturing infra-red images of the tissue and/or cellular structures of the target site and nerve(s) to be treated. In a particular instance, the image-capturing device may be a camera, such as a complementary metal-oxide semiconductor, CMOS, camera, that is capable of generating a three-dimensional image of the treatment nerve(s) at the treatment site.

Hence, once the treatment sight has been scanned a 3-D topographical map of the site may be generated, then the appropriate nerve tissue can be identified, and the dimensionality of the nerve to be treated, with respect to its surrounding tissues and structures and/or distance of device from the target and/or treatment sites, can be identified, and the treatment site and/or application distance can be clearly demarcated and bounded. With such mapping the automated positioning element and magnetic flux delivery vehicle, e.g., tMS device, can be precisely targeted, such as with respect to depth, angle, orientation, and the like, so as to deliver treatment to the nerve cell with pinpoint accuracy and fine-tuned repeatability over a number of different treatment days.

For instance, the automated positioning element and/or tMS device may include an orientation sensor that is capable of determining an orientation of a component of the system, such as the tMS device, and/or may include a pressure sensor, such as for sensing forces in a plurality, e.g., all, directions, such as a force torque sensor. The system may also include a time of flight sensor, such as in conjunction with, or otherwise coupled to, the visioning system. In various instances, the positioning of the positioning element may be controlled manually, e.g., by an operator, or may be controlled automatically by the system. Likewise, the system may be configured for retracting the positioning element if there is something that gets in the way of its movements, its imaging, and or the application of the tMS device, or if it senses the presence of an aberrant or harmful condition.

Configuring the system to autonomously control the positioning of the treatment apparatus cuts down on time and cost and unpredictability inherent to having a technician controlling the operations thereof, and can increase safety. This is important because of the nature of the A-β nerve fibers that are very sensitive to touch such that even slight, gentle contact with the target site can cause an intense experience of pain. In various embodiments, the subject themselves can autopilot the positioning elements of the system, so as to self-administer the treatment. In various instances, the system including the visioning and application modules can be configured to target, manipulate, and adjust the system components, such as with respect to position, distance, and orientation of the device vis a vis the target site, and can constantly be checking and double checking one or more of these conditions, such a 100 or 200 or 400 or 500 or 1000 or more times a second, such as via the vision and orientation sensor systems, for instance, time of flight Accordingly, in various embodiments, presented herein is a therapeutic system and method for treating chronic pain, which system and methodology boasts a variety of unique components and features that individually and in combination demarcate an exceptional advancement in the art. For instance, as can be seen with respect to FIG. 1, in various embodiments, the pain treatment system may include one or more of the following components: a magnetic induction device 10, e.g., including a magnetic coil 15, an image capturing device 30, a positioning element 20, one or more sensors 60, a system controller 70, a remote server 80, and one or more control switches.

Particularly, the pain treatment system 1 may include a magnetic induction arrangement. The magnetic induction arrangement 5 may include a control unit 70 and a source for generating a magnetic field 10. Any source for generating a focused magnetic field may be used. In various instances, the source may include a magnetic coil 15, such as a coil having a plurality of coil interfaces, e.g., 15a and 15b. For instance, the magnetic coil 15 may be configured as a figure eight or a butterfly coil. In various instances, the magnetic induction device 15 may be configured as a stimulatory device that is configured for generating a focused magnetic field, which in turn is capable of generating a concomitant electrical current, such as within a nerve tissue. In a particular instance, the magnetic induction arrangement is a transcutaneous magnetic stimulation (tMS) device 15. Likewise, the control unit 70 may be any mechanism configured for generating and controlling the energy sufficient to allow the magnetic coil to generate the magnetic field.

Further, in various embodiments, the system 1 may include a positioning element 20 that is configured for positioning and/or orienting a magnetic stimulatory device 10 proximate a treatment site of a subject, such as a subject experiencing pain and/or in need of treatment. The positioning element 20 may be any device that is capable of moving, positioning, and orienting a stimulatory element, e.g., tMS device 10, in proximity of a nerve, such as a nerve radiating pain, so as to generate a magnetic field, which magnetic field is capable of creating an electric pulse in the targeted nerve cell that is sufficient to depolarize the nerve, thereby activating the nerve, and causing a cessation of pain.

For instance, in various instances, the positioning element 20 may be an articulating arm device, such as an arm that is composed of several segments 20a, 20b that may be coupled together via one or more moveable joints, which joints may include one or more motors 21a, 21b, 21c, such as a moveable joint and/or motor(s) that allows the arm to move or otherwise articulate along one or more planes, such as along one or more of an X, Y, or Z plane. In particular instances, the one or more motors may be configured for facilitating the movements of one or more arm segments along one or more X, Y, and Z planes, and may further facilitate movement along an X, Y, or Z axis. Accordingly, in various embodiments, the positioning element may be moved manually and/or autonomously.

Accordingly, in various instances, the positioning element 20 may include a control unit, such as a control unit that is in communication with the one or more joint motors 21 and is configured for articulating the positioning element 20 and/or one or more portions of the element 20a, 20b. Specifically, where the positioning element is an articulating arm 20 composed of a plurality of segments 20a, 20b coupled together via one or more motors 21, the control unit may be configured to send commands to the motors so as to control their activation and thereby control the motions of the segments of the arms, such as horizontal movement along an X plane, or vertical movement along a Y plane, or diagonal movement along a Z, and/or rotational movement around an X, Y, and/or Z axis. In various instances, one or more motors of a plurality of arm segments of the positioning element may be configured for directing orthogonal movement of the positioning element.

In various embodiments, the positioning element 20, e.g., the articulating arm, may be configured to be manually articulated, and/or therefore may be manually positioned. However, in other embodiments, the positioning element 20 may be configured for being positioned automatically or semi-automatically. For example, in particular instances, the movements of the articulating arm 20, or other positioning element, may be controlled by a central controller 70, such as a controller 70 that is configured for controlling the various motors 21 of the positioning element 20 so as to direct its movements in three-dimensional space. Accordingly, the positioning element may be a robotic arm 20 that is not only configured for being moved in a planar manner in 3-D space, but is also capable of rotating about each central axis, such as automatically or otherwise autonomously.

Additionally, the system 1 may include an imaging unit having an image capturing component 30, which component may have a camera for capturing images, for instance, for taking pictures or video. For example, an imaging unit may be included as part of the system, such as where the imaging unit is configured for imaging one or more spaces, such as the interior or exterior space in which the subject is occupying and/or the exterior space in which an included positioning element is moving or capable of moving.

Particularly, the system 1 may include an imaging unit 30 such as for determining where and in what orientation the positioning element 20 is in space, where and in what orientation the magnetic induction element 10 is in, and/or where and in what orientation the subject, or a part of their body is in, such as a part of their body to be treated. In some instances, the imaging component may be configured for determining the relative positions of the various elements of the system 1. Specifically, the imaging unit 30 may be configured for determining where the magnetic induction element 10 is relative to a targeted treatment site on the body part of the subject being treated.

For instance, in various embodiments, the imaging unit 30 may include a plurality of cameras 30a, 30b, which cameras are configured for defining a three-dimensional space in which the positioning element is moving, and/or for defining a three-dimensional space occupied by the patient, and for moving and orienting the positioning element 20 relative to the body part being treated so that the magnetic induction device 10 may be brought into proximity and orientation of the body so as to efficiently deliver a magnetic field to the body part. Particularly, in certain embodiments, the imaging unit 30 may be configured as a stereoscopic camera that is adapted for capturing images, such as 3-D images of a given space in which the positioning element 20 operates. In various embodiments, the imaging component, such as the camera 30, e.g., the stereoscopic camera, may include one or more lenses 30a, 30b, such as a plurality of lenses having a determined focal length.

Additionally, in particular embodiments, the imaging unit 30 may include a light source 40, such as for illuminating an area, for taking a measurement, determining a distance, and the like. The light source 40 may be a plurality of light sources such as a collection of light emitting diodes (LEDs). The LED lights 40 may be positioned on the imaging unit, such as on or around the imaging component and/or the camera lenses. For instance, one or more of the light sources may be positioned proximate a circumference of at least one of the camera and/or the camera lenses, such as including 2, 3, 4, 5, 6, or more lighting sources that may be positioned proximate a circumference of one or more lenses. In a particular embodiment, the lighting source may include LED lights may be configured for emitting a light wave in the infrared spectrum, such as for use in determining movement in a defined 3-dimensional space and/or for determining one or more distances or orientations therein, and/or for determining a speed, acceleration, or direction of motion.

Further still, another component that may be included as part of the system is one or more sensor modules 60 such as including one or more sensors 60a, 60b. For instance, a sensor module 60 may be included such as where the sensor module includes a distance sensor 60, such as a sensor that is configured for determining the distance between one or more of the positioning element 20, the magnetic induction unit 10, and the target site on the subject to be treated. Specifically, a distance sensor 60 of the system may be any element that is configured to detect or otherwise determine the distance between two objects. This determination may be made by a calculation of distance over time, such as by calculating the time it takes for a sound or light wave to travel to and/or back between the sensor and an object. For example, the distance sensor 60 may be a unit that is configured for emitting a sound or light wave, such as a laser, which wave travels to and/or back from an object, such as a reflective object at a known velocity, and from the time it takes to make this journey the distance to the object may be determined. Accordingly, in a particular embodiment, the distance sensor 60 may include a laser, such as a micro laser distance scanner.

A motion or pressure sensor may also be included. For instance, a sensor configured for determining contact or near contact between the subject being treated and the treatment device, such as the positioning element and/or the magnetic induction element, may be included and configured such that when a contact occurs or is expected to occur, the treatment device may be withdrawn so as to minimize or entirely avoid such contact. Particularly, the active site of the subject being treated may be very reactive to touch. So being the treatment device may include one or more sensors that are configured to determine the movements of the subject, to track the movements, to characterize the movements, such as with respect to speed, direction, orientation, and the like, and in response thereto one or more of the motors of the device can be activated so as to effectuate the tracking of the device to the subject's movements and/or withdrawal of the device away from the subject if contact is made or expected to be made. In a particular embodiment, the sensor may be a torque-force sensor that is configured for withdrawing the positioning element and/or magnetic induction device if contact is experienced or suspected to occur.

Additionally, the system 1 may include one or more computer 70 or server 80 systems. Particularly, the various components of the system 1 may be communicably coupled one to another and to a computer 70 and/or server of the system 80, such as in a wired or wireless configuration, such as via a network 90, such as via a private or public network, e.g., the Internet. For instance, in various embodiments, the system 1 may include a computer 70 and/or a server 80, such as a local computing resource, such as for controlling the local functioning of the system components, and a remote cloud-based server, such as a server in connection with a plurality of local computing resources, where one or more of the local or remote computing resources may be coupled to a memory and/or external database.

Specifically, in particular embodiments, a cloud-based server 80 may be included. For instance, a cloud-based server system 80 may be provided such as for storing and/or processing data, such as data pertaining to one or more subjects. The server system 80 may be configured for receiving data directly from one or more of the positioning element 20 and/or the magnetic induction device 10, or the server system 80 may receive data indirectly from a local computing resource 70 that is itself coupled to the positioning element 20 and/or the magnetic induction device 10 and/or the imaging component 40, all of which may be in communication one with the other. Specifically, in one embodiment, the local computing resource 70 may be a desktop computer, laptop computer, tablet computer, smart phone computing device, and the like. Likewise, the remote server system 80 may include a LINUX® server having a plurality, e.g., 6, 12, 18, 24 or more CPUs or GPUs, which CPUs and GPUs may be coupled to a suitably configurable FPGA that is adapted for performing one or more of the analyses and/or processing operations disclosed herein.

In certain instances, the system 1 may include a remote server 80 that includes a plurality of different computing instances, such as a CPU, GPU, and/or an FPGA, ASIC, and the like, and as such, any of these instances can be configured for implementing one or more methods of the system. Where an FPGA is provided, the FPGA(s) may be adapted for being reconfigured, such as partially reconfigured, between one or more of the various steps of implementing one or more of the system parameters. In various embodiments, the local computing resource 70 and/or the remote server 80 may be configured for assisting in the running the various components of the system 1 and/or for collecting data pertaining to the operations of the components and/or data pertaining to the treatment of one or more subjects.

One or more of the local computing resource 70 and the server system 80 may be configured for running one or more analytics on the collected and/or stored data. Hence, using a local computing resource or another, remote client computer the cloud accessible server system and/or a storage device thereof may be accessed, such as for the storage and/or analysis of data. For example, a remote user may access the system so as to input patient data, e.g., treatment data, into the system, such as for storage and/or the processing thereof. Particularly, a remote user of the system, e.g., using local computing resource, may access the server system so as to upload patient data, e.g., such as one or more treatment parameters or results thereof of one or more individuals. In various embodiments, the system may include a user interface, e.g., accessing a suitably configured application programming interface, API, which will allow a user to access the server so as to upload data to be processed, control the parameters of the processing, direct system configurations, and/or download output, e.g., results data, from the system.

In particular embodiments, the local or remote computing resource may include a workflow management controller that is configured to control one or more aspects of the system, such as locally and/or globally, e.g., system wide.

In various instances, the system and/or a component thereof may include a communications module, which communication module may include one or more communications devices such as for providing a communicable link between two or more components of the system. For instance, a communications device may include a transmitter and/or a receiver, such as including one or more of a radio frequency (RF) transmitter, a cellular transmitter, a WIFI transmitter, and a Bluetooth or Low Energy Bluetooth transmitter that is adapted in a manner so as to allow a suitably configured component of the system to be accessible wirelessly and/or remotely. In some instances, a typical receiver may include a satellite based geolocation system or other mechanism for determining the position of an object in three-dimensional space. For instance, the geolocation system may include one or more technologies such as a Global Navigation Satellite System (GNSS). Exemplary GNSS systems that enable accurate geolocation can include GPS in the United States, Globalnaya navigatsionnaya sputnikovaya sistema (GLONASS) in Russia, Galileo in the European Union, and/or BeiDou System (BDS) in China.

In various embodiments, the system may include one or more safety monitors and/or shutoff mechanisms such as for determining if and when a safety risk may arise, and upon such a condition may function to withdraw the system components from the treatment site, power down, and/or shutoff the system. In particular embodiments, the safety mechanism may be configured as a safety command device, such as an electric or mechanical switch mechanism for retracting the magnetic induction device and/or positioning element and/or for shutting down one or more of the system components.

Accordingly, in various embodiments, a system is provided for manually and/or automatically providing one or more therapeutic and/or prophylactic treatments to a subject at risk of suffering from pain, such as acute and/or chronic pain. As indicated above, and as seen in FIG. 1B the system 1 may include a transcutaneous magnetic stimulation (tMS) device 10. The tMS device may be configured for directing a low and/or medium, and/or high frequency magnetic field toward a determined treatment area. For instance, in various embodiments, the tMS device operates within a frequency range from approximately 0.2 Hz to about 5 Hz. Specifically, the frequency range may be divided into a low frequency stimulation range from approximately 0.2 Hz-1 Hz and a high frequency range from approximately 1 Hz to 5 Hz. Particularly, the tMS device 10 may provide a pulse having a varying magnetic pulse field strength and/or varying voltage. For example, the magnetic pulse field strength has a continuous stimulation capacity of up to about 1 to about 3 to about 5 or more Tesla. In various instances, the waveform produced may be a single or a biphasic waveform. In particular instances, the waveform may be biphasic waveform that is effective with regard to the threshold of excitation and response amplitude of the underlying nerve receiving the magnetic pulse.

In particular embodiments, the tMS device may include a housing 11 that is configured for allowing the tMS device to be handheld, and in other instances the tMS device housing is configured for being coupled to a positioning element 20, such as for being coupled to a robotic arm. In various instances, the housing may be of any suitable size and/or configuration, but in particular instances, the tMS housing measures approximately 3 to 5 to about 10 inches in length, approximately 1 to 2.5 to about 5 or more inches wide, and approximately 0.5 to 1.5 to about 3 inches deep. Where a handle portion of the device is provided, the handle portion of the tMS device may extend approximately 3 to about 5 or about 7.5 to about 10 inches from the coil portion, and may be adapted to allow for the tMS device to be handheld or mounted during use.

The tMS stimulator 10 may be configured for generating a magnetic flux or field that in turn produces small electrical currents around a neuroma or nerve entrapment, and can be applied without anesthetics. In certain instances, the tMS device includes a magnetic coil 15 that may be an insulated, whereby the magnetic coil can be held over a target and/or treatment area either with or without contacting the affected area. In various instances, the tMS device is positioned so as to not touch the target or treatment area. This method of pain neuromodulation provides a major advantage in treating patients with increased sensitivity to non-noxious stimuli (allodynia), for instance, as the treatment does not require direct device-patient contact or direct tissue penetration. Accordingly, the dynamic magnetic flux produced by the tMS device may be configured to induce neuronal stimulation in a more focused manner than can be generated by other direct current stimulation modalities, such as a transcutaneous electrical nerves stimulator (TENS).

Hence, the tMS device 10 is configured for delivering a directed a magnetic flux to a target and/or treatment area. Specifically, when a current is passed around the coil 15, a dynamic magnetic flux will pass through the skin and into a selected depth, such as a first few centimeters depth of the skin, which may be delivered without attenuation. In various instances, the tMS device may be configured to effectuate a treatment whereby the current required is decreased from approximately 1200V to about 700V. Particularly, the tMS device is configured to produce a focused dynamic magnetic flux from the center of the coil 15 to the target and/or treatment site which can be marked, e.g., in any suitable manner, such as with an extended optical cross-hair in order to target a specific area on the body. In one embodiment, the coil 15 may have a magnetic core of permalloy, Mu-metal, or other ferromagnetic compound, which may be assembled in the center of the coil to further increase the strength of the magnetic flux. In one embodiment, the magnetic core is shaped into a figure-of-eight coil 15 that includes a left coil 15a and right coil 15b.

More particularly, the figure-of-eight coil 15 may rotate internally up to approximately 30 degrees in order to adjust a focal point of the treatment by redirecting the magnetic field. Specifically, in various instances, the focal point may be focused to within approximately 3-5 millimeters in the rotated configuration. For instance, the magnetic coil 15 may be configured to rotate the configuration of the figure-of-eight coil, which may be rotated via a central gear mechanism attached to a curved mounting piece. More specifically, the curved mounting pieces may be metal pieces that are attached to the coils via screws or any other practical attachment mechanism. The gear mechanism may be driven by a small motor attached with a central gear, such as where one or more of the coils may be connected with the gear mechanism through a single secondary gear. The opposing coil, therefore, may be connected with the gear mechanism through two or more secondary gears so as to effectuate an opposite direction of rotation of the coils so that they both rotate inward to focus on a single target point. This rotated configuration occurs through the motor actuating the gears to rotate the coil via the mounting pieces.

In various embodiments, the system 1, and specifically, the tMS device 10 may include a light source, such as an LED. The light source may be positioned on an application side of the coil portion that faces the body, so as to guide a center of magnetic flux generated by the coil to a target and/or treatment area and site. The tMS device, and/or an associated positioning element 20, may also include a motion sensor, such as an accelerometer and/or gyroscope, which may be configured to detect motion, direction, magnitude, and/or velocity of the motion of the tMS device and/or positioning element. In various instances, the sensor may be able to detect motion and acceleration as well as to sense orientation, vibration, shock, pressure, and/or contact, such as for the purpose of withdrawing and/or turning off the device during deviations from treatment locale.

For instance, a magnetometer may also be included to measure the strength and direction of one or more magnetic fields generated by the stimulation coils 15 to optimize accuracy and intensity of treatments. Further, a proximity sensor may be included to detect and confirm that the target region and/or treatment area is within the appropriate range of the tMS stimulator 10 to precisely deliver treatment to achieve the greatest results. Likewise, the tMS device 10 may be designed with a thermode or other control switch so as to automatically shut off the stimulation device in the event of overheating from both internal and external factors. Particularly, in a particular embodiment, the tMS device 10 may be coupled to a controller, where by for efficiency, the controller software of the controller may utilize a negative-feedback method so as to detect unusual heating patterns to prevent damage to the device, or injury to the operator or patient, by warning them and turning off the device.

The circuit design for operating the tMS device has been configured so as to optimize efficiency. For instance, the circuitry may be adapted to continuously monitor and adjust power outputs to ensure efficacy of the treatment and safety of the user. Crucial circuit components may be tested in every power cycle, before and after each treatment administration with the primary hardware supervisory circuits and secondary software monitoring systems in communication with the control components of the system, including control unit 70. Particularly, the circuitry may be configured to boot, e.g., in stages, and if a failure is detected, a safety interrupt may be implemented so as to discontinue the booting process, shutdown device operation, and ask for servicing. The circuitry inside the controller, if included in the tMS device, may also include parallel high voltage chargers, such as where each is capable of up to 1600 or more watt power output, energizing capacitor banks, with up to 2200 or more uF energy storage capacity, and discharging hardware to decrease loss of performance and increase reliability. In various instances, the capacitor bank inside control module may range in voltages from −2000 to +4500 volts DC or more in order to conserve energy and optimize performance. The repetitive controllable on-state current within the controller and stimulation coil 15 may reach up to 4000 volts DC or more. In one embodiment, multiple high power converting thyristors may be stacked to achieve the performance requirements of this pulsed power application. Heat from inductance may be managed internally with small, electrically powered, forced-air cooling systems, such as utilizing continuous duty DC blower fans, e.g., operating at up to 5200 RPM or more. In one embodiment, the system 1, positioning element 20, and/or tMS device 10 can be password- or biometrically-protected to ensure access only by approved users of the device.

Figure 1B:
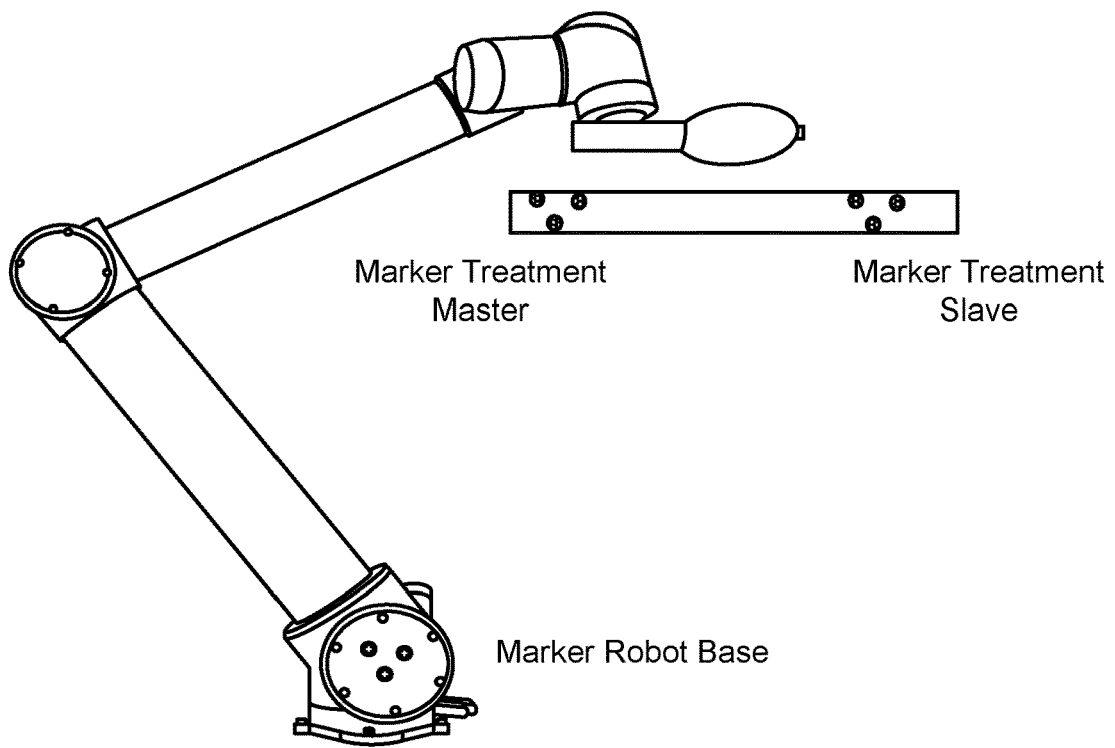
FIG. 1B provides an illustration of an exemplary positioning element and transcutaneous magnetic stimulatory (tMS) device of the disclosure.

As set forth in FIG. 1, the system may include a control module 70 that is configured for controlling the operations of one or more of the components of the system 1. For instance, the control module 70 may include a computing system, such as a desktop or laptop computer, etc. that is in wired or wireless communication, e.g., via a wireless network interface, with one or more of the tMS device 10, the positioning element 20, the imaging component 30, one or more sensors of the system, a lighting element 40, and/or a cloud-based server system. The control module 70 may further be in communication with a controller of the positioning element 20 and/or one or more of the motors thereof. In particular embodiments, the control module 70 is configured with hardware and software to precisely control the tMS stimulator 10 and/or positioning element 20 so as to provide instructions and/or receive feedback relating to the treatment, such as in real-time and post-treatment.

The control module may be controlled by any suitable mechanism such as via one or more control instruments, e.g., a button, toggle, switch, and the like, or may have a touchscreen interface, such as a touch-sensitive capacitive touch-screen display, through which control instruments the settings of the control module may be adjusted. In various instances, the touchscreen display may present tMS device information or connection status indications pertaining to connections with the system components or another network device. For instance, the control module may display the controls for modulating the pulse width, amplitude and frequency of the treatment, and may be configured for displaying real-time signal data on the applied fields, all of which may be controlled via a control instrument of the control module, or may be controlled such as via a downloadable client application that runs on a mobile computing device, such as a smart phone. Specifically, the control module may be configured for controlling the positioning of the positioning element 20 components, the orientation of the tMS device 10, and/or an output of the tMS device. For example, in a particular embodiment, a suitable output of the tMS device may be 3 T at 1 Hz, with 20 KTesla/sec instantaneous flux. However, in other embodiments, the output may be a reduced output such as at approximately 1.5 Tesla and 3 pulses per second (PPS). Further, in particular instances, the system 1 may be configured for in-home use, such as where a suitable output may be approximately 3 Tesla and 5 PPS, where as in a clinical setting, the clinical tMS device may be capable of outputting approximately 4 Tesla and 50 PPS.

Accordingly, in various instances, the system 1 may include one or more components that may be controlled by one or more internal controllers, and/or the system may include a control module 70 that is separate device from the treatment delivery components. In either instance, a control mechanism of the system may be configured for performing one or more of the following: directing delivery of a specified pulse characteristic, e.g., rate; determining a particular magnetic field characteristic, e.g., having a specified strength; determining a suitable target and/or treatment area; controlling the positioning of the positioning element and/or tMS device; and directing the tMS device to deliver one or more pulses at specified rate and strength. As indicated, the control module 70 may be in a wired or wireless configuration.

For example, the control module 70 may include a wireless transmitter/receiver and corresponding software to provide a wireless connection with another component of the system. Particularly, the control module 70 may be in communication with one or more sensors of the system so as to track the movements and/or functionings of the components of the system. In this manner, the controllers of the system may act in concert to manage the application of one or more treatments to a subject, e.g., a patient, in need thereof.

Likewise, as indicated, one or more of the controllers of the system may be configured for receiving command instructions, e.g., via a remote client application running on a computing device of a remote operator, such as for remotely programming treatment parameters, troubleshooting assistance, updating software, and to ensure compliance. Accordingly, in an exemplary embodiment, the controllers of the system may be equipped with a communications device, such as BLUETOOTH®, e.g., low energy BLUETOOTH® 4.0 technology, which provides connection to one or more other controllers, a cloud based server 80, and/or a remote computing mobile device, e.g., a smart phone or tablet computer, for tracking and managing treatment, patient feedback, and results, so as to optimize therapeutic parameters and maximize analgesic efficacy. In various instances, a component of the system, such as a control module 70 may be configured so as to be powered by AC or DC electricity or a rechargeable battery. In one embodiment, the control module may be equipped with rechargeable batteries (Lithium-ion & Sodium-ion) or graphene supercapacitors to increase mobility.

As discussed above, the control module 70 may have a display screen 72, which display screen may be a capacitive sensing touch-screen display, for allowing a system operator to configure the various system components, such as to adjust the various settings of the tMS stimulator 10. Likewise, the tMS device may be controlled through the control module 70, or may itself include control buttons for controlling the settings and other parameters of the device. In either instance, one or more control instruments for controlling the settings of the tMS device 10 may be provided, or a touch sensitive display screen may be provided for controlling the settings and displaying various status and other indicators.

Particularly, as described in greater detail herein below, a graphical user interface (GUI), such as for configuring and controlling the system, may be accessed via the display, such as where the display is a capacitive-sensing touchscreen display. The GUI may be presented at the control module 70 or a third party control device, such as a display may be on a client computing device, such as a smartphone. The GUI allows the user, e.g., a system operator or patient, to input the settings for their treatments and provide a pre-treatment pain score and post-treatment pain score. The scores can then be correlated with the input settings to determine which tMS settings provide the best reduction in pain. Additional feedback from the subject to be treated relating to the treatment may be entered automatically, e.g., via voice recognition, or by the system operator manually entering in to a notes tab.

Likewise, as indicated, the display screen may be configured for displaying information on the positioning of the components of the system and information regarding the treatments being administered. For instance, the system may determine, and the display may present a screen depicting where all of the components our in space relative to one another, and/or may display tracking information so as to account for relative motion of the components relative to that space, such as a tracking distance to a target region. Likewise, the display at the GUI may present treatment parameters related to the tMS settings. As indicated, the display screen, and representations of the buttons presented therein, may be capacitive touch or capable of receiving other touch inputs, so that the user can select the levels of the tMS device settings, including: frequency, duration, pulses, and amplitude.

As discussed, these settings may be entered at a controller of the tMS device 10 or may be entered at a separate control module 70. In either instance, the control device may be configured for communicating these setting selections automatically from one to other components of the system, and may be presented for display thereby. For instance, the tMS device 10 may automatically transmit the current settings, during and/or after a treatment session so the operator or patient can instantly provide feedback related to the session, which feedback can be entered manually or automatically into the system 1.

Accordingly, the graphical user interface may also allow the user to control the tMS device 10 for executing a treatment session. For instance, a pain score interface may be displayed where the user inputs a pre-treatment pain score. Likewise, the interface allows the patient to input a post-treatment pain score. The differences between scores can then be compared with the settings for the particular treatment to determine how effective the treatment was at the particular settings. The operator or patient may add notes to further explain the reasons for the scores or other information relevant to the treatment, and these notes may be transmitted to a healthcare professional along with the treatment settings and pain scores, as will be described in further detail below. Hence, as described below, the system 1 may be configured for receiving feedback, and making adjustment to system parameters with respect thereto.

Additionally, not only may the system 1 be configured for receiving operator or patient feedback, it may be configured for receiving component feedback. For instance, the system 1 may include one or more feedback devices. For instance, a feedback device may be a portable signaling device that may be configured to be positioned on a moveable component of the system and/or on or near a target site, for signaling to the system 1, where the components are and/or where a treatment area is. In various embodiments, the feedback device may be an electronic signaling device, whereas in other embodiments, it may simply be a reflective device. For example, in certain embodiments, the feedback device may be a portable electronic device that is configured for receiving data from the control module 60 and/or imaging component 30 relating to the delivered magnetic pulse and/or direction of transmission, and to generate feedback with respect thereto. The system 1 may receive this data and correlate it with data received from a subject relating to the delivered magnetic pulse, such as data rating the subject's experience of pain and/or its amelioration at the treatment area and/or at one or more treatment sites.

Hence, the feedback device may be configured for wireless communication with one or more controllers of the system, such as the control module, and thus, may be configured for receiving, generating, and transmitting feedback, which feedback may be used by the system to change of modulate one or more control settings, such as relating to a treatment parameters. For instance, in one embodiment, the portable electronic feedback device may be utilized with the tMS device 10 and control module 60 to provide for wireless control of the tMS device 10 and analysis of treatments.

In particular instances, the system may be configured for receiving one or more constructions from a third party computing device that may be in communication with one or more components of the system. For example, a third party computing device may be a remote device that communicates with the control module 70 of the system, and as such may be a mobile computing device, such as a laptop computer, a tablet computer or smart phone, or even a smart wearable device. Accordingly, the third party computing device may be configured to wirelessly communicate with the control module 70 and/or positioning element 20 and/or tMS device 10, so as to provide control instructions to one or more system components. Particularly, the third party computing device may include a display, e.g., a GUI, that is configured for providing a visual interface for displaying information about the control of the system components, treatments performed thereby, and provide for inputs for the operator or patient to interact with the system components. The third party control device, along with the feedback device, may be connected one with the other and/or to the system through a suitably configured communications interface, such as via a wireless connection protocol, such as Bluetooth®, Wi-Fi®, NFC, or a proprietary device-specific network such as the 2net™ Platform® for wireless health, and the like. In one embodiment, an internal modem with an omnidirectional antenna may be utilized to connect with IEEE 802.16 family wireless hotspots and 3G telecommunications networks such as WiMAX. These networks may be utilized to passively transmit usage data on the device to a remote server for monitoring the usage and performance of the device. Updates to the settings, programs and configuration of the hardware, software and firmware may be provided over these networks, whether by a technician who is improving the performance of the device or by a physician updating a patient's treatment session parameters.

In various embodiments, the system 1 may include a guidance tool. Specifically, in various embodiments, guidance for proper positioning of the target region, such as for identification of one or more treatment areas, can be provided by one or more, e.g., a combination, of marking elements that may be applied to the subject's skin, e.g., approximate a target region. As explained below, the guidance tool may be a distinct, physical element that may be positioned on or near the target area, or it may simply be a mark provided by a marking material that is visible or invisible or nearly-invisible under normal light conditions. For example, a fluorescent ink may be used, such as where the ink is visible only under focused UV light, e.g., a black light. In such an instance, the imaging component may include a UV light source, which light source is optically focused to coincide with one or more optimal flux locations from the stimulation device. In one embodiment, the UV light source may be an LED that produces light at around 400 nm, making it more compact, rugged and easily portable, while generating light that is near the lower end of UV wavelengths and, therefore, safer for repeated exposure.

In other embodiments, guidance may be provided by a tool for use in determining the relative positioning of one or more of components of the system, such as for determining the relative position of the positioning element 20 and/or the tMS device 10 with respect to the treatment area, including one or more treatment sites, of the body. Particularly, in various embodiments, a guidance tool may be provided such as where the guidance tool includes one or more demarcation elements, such as a locating component, e.g., a light element, such as a light emitting diode, capable of being tracked, a measurement sensor, such as for measuring distance, and/or reflective element, so as to form a guidance matrix. For example, the guidance tool may be one or more of a light emitting or reflective marking device. The light emitting and/or reflective marking device may be any element that includes one or more light emitting or reflective elements that is capable of being positioned in such a manner as to define or otherwise demarcate the location or position of a treatment site, positioning element, and/or a magnetic coil of the system.

In a particular embodiment, the light emitting and/or reflective marking device includes one or more extended members, such as a plurality of opposed extended arm members. Specifically, in various embodiments, the marking device includes a plurality of arm members, such as where each arm member includes a proximal portion having a proximal end and a distal portion having a distal end. The arm members may be configured for being coupled to one another at their proximal ends, such as to form the configuration of an "X". Additionally, the marking device may include a light emitting and/or reflective element positioned proximate the distal end of each arm member. In such an embodiment, the marking device may be configured for being positioned at a target site that is proximal a location to be treated. In various embodiments, the marking device may be configured to aid in one or more of the positioning of the various components of the system with respect to one another, e.g., vis a vis the targeting and/or treatment site, and may further aid in determining a quality and/or directionality of the magnetic flux to be delivered by the magnetic coil.

In various instances, the system 1 may be configured for not only administering a treatment regime, including a series of magnetic induction administrations, but the system may also be configured for collecting, analyzing, and/or tracking data. For instance, as indicated, the system 1 may include a computer or server, such as a local computing resource 70 or a remote cloud-based server 80, that is communicably coupled to a database, such as a database that is configured for storing patient data, such as for determining, monitoring, and tracking data about one or more patients.

Accordingly, in various embodiments, a system 1 for delivering magnetic induction, e.g., in the form of a treatment, such as by using a tMS device 10 as disclosed herein is provided. Hence, the portable electronic tMS device 10 may include a communications module such as for communicating both with a controller of the device, a local computing resource 70 in communication with the controller, and in various instances with a remote server 80. The system, therefore, may be configured for treating a subject and communicating the data related thereto to one or more computing resources, e.g., remotely and/or locally, where the data to be collected and transferred may be related to the patient and/or malady, e.g., pain to be treated, one or more characteristics about the treatment session, patient feedback about the treatment and its administration parameters, such as device settings, magnetic wave dimensionality: frequency, amplitude, intensity, the configuration of the system, orientation of the positioning element and/or its segments, e.g., its coordinates in 3-D space and/or its rotations, orientation of the magnetic coil device, information regarding the treatment and/or target site, its location in 3D space, the dimensionality of the treatment site, treatment depth, device settings, and the like. All of this data can be collected and can be transmitted to the local 70 or remote 80 computing source, such as for storage and/or analysis.

In various embodiments, the data received at the remote server 80 may be stored in a database 81, where the data for individual subjects, e.g., patients, or a group of subjects or other users, may be collected and analyzed to determine the effectiveness of treatments on certain types of subjects, body parts, treatment sites, pain, symptoms, etc. Likewise, the remote server 80 and/or local computing resource 70 may also be configured to transmit data to the tMS controller or magnetic delivery device 10. For instance, such data to be transferred back and forth between the various devices of the system include one or more of treatment settings, treatment configurations, including distances and orientations, and the like. This data can be transmitted back and forth in order to provide current, updated, real-time treatment plans and settings based on the patient feedback, thus avoiding the need for the patient to visit the same healthcare provider at the same location, but rather, can visit any location anywhere in the world based on the collected data from previous treatments.

For example, in various embodiments, the system 1 may include an application programming interface, API, so as to allow other systems to access and configure the tMS system components, and/or to configure the tMS system itself. In a manner such as this, a nationwide server system may be established whereby subject data from a plurality of remote treatments sites may be collected, correlated based on one or more factors, such as treatment site, quality of pain, effectiveness of treatment, treatment parameters and the like, which correlated and analyzed data may then be used to configure the system. This data may be collected and analyzed, such as by a suitably configured A/I module of the system, so as to determine optimal treatment parameters, for instance, based on a statistical analysis of a plurality of patients being treated. Optimal treatment parameters may be determined such as based on the treatment for similar pain from similar conditions such as from similar treatment sites, where the system has determined that various system parameters and configurations have been identified as having efficacy in a statistically effective manner, such as by being effective for the treatment of 75%, 80%, 85%, 90%, 95%, 98% of subjects having common characteristics as to quality of pain. Accordingly, the system may be configured for receiving a plurality of data from a plurality of treatment locations for a plurality of subjects being treated over a plurality of sessions, and for analyzing that data to determine optimal treatment characteristics and procedures, which optimal procedures may then be communicated back to the local tMS systems so as to calibrate and set the local parameters for treatment based on the identifiable pain and/or treatment site characteristics and the like.

Another component of the system, therefore, may be a workflow manager system (WMS), which may include an API configuration, wherein the WMS is configured for assessing incoming treatment requests, indexes one or more treatment jobs to be performed, forms a queue, allocates the resources, e.g., tMS device allocation, and generates a pipeline for treatment flow, such as where a central facility is controlling the operation of a multiplicity of local tMS systems. Accordingly, when a request for treatment comes in to the system 1, either for local or remote treatment, and is preprocessed and queued, an instance, e.g., computing resource, allocator may then spin up the various treatment job devices in accordance with the queued treatment projects. Hence, once the various treatment projects are indexed, queued, and/or stored in an appropriate database, the WMS will then pull the determined optimal treatment data from storage, cycle up an appropriate instance, which retrieves a treatment file for the subject, such as based on a characterization of their pain, or a previous treatment regime, and may then run the appropriate processes on the data to perform one or more of the requested treatment jobs.

Likewise, once the treatment has been performed and/or feed back from the subject regarding the treatment has been obtained, then the results data may be collected, compressed, if desired, and stored, such as in an appropriate memory instance, e.g., a first data base. These results data may then be analyzed by the system and one or more new treatment parameters may be determined and used to adjust the optimal treatment parameters, which new optimal treatment parameters may then be used for the next treatment regime to be administered to the same or a new patient. Further, as new treatment requests come in and/or current jobs are being run, the workflow management system will constantly be updating the queue and optimal treatment parameters (real time) so as to continuously be updating the various different tMS devices of the entire system 1 so that at any given time any given tMS device 10 may be implementing the most up to date treatment parameters, so as to keep the data flowing through the system and the processes of the system running efficiently. Accordingly, the system 1 may constantly be taking the results data and storing the data in a local and/or a remote database, prior to further processing and/or transmission, such as transmission back to the central server 80. The generated results data files when compressed and/or stored may include appropriate meta data and/or other associated data, which associated data may be different for data to be stored versus data as it flows through the system.

Accordingly, the devices and systems presented herein may be implemented for the purposes of effectuating one or more, e.g., a variety of, treatment protocols. For instance, the devices and systems of the disclosure may be employed for the purpose of treating pain, such as chronic pain, for instance, chronic pain caused by damage or other injury to one or more nerves. Specifically, in an exemplary method, the devices and systems of the disclosure may be configured for treating neuropathic pain, such as for providing tMS to a treatment site experiencing pain.

Particularly, in a first step, a tMS system 1 including a tMS device 10 may be provided, such as for the administration of therapeutic treatments. The tMS system, as disclosed with respect to FIG. 1, may include a control module 70, a tMS device 10 having a magnetic induction apparatus 15, a positioning element 20, an imaging or tracking component 30, and/or one or more other components of the system disclosed herein. Once provided, the device operation settings of the control module may be configured, manually or automatically, such as in accordance with determined optimal administration parameters, for a treatment session. The treatment parameters may be determined, as discussed above, and may be specific to the subject to be treated, and may include the frequency, duration, pulse, and amplitude, of the tMS device, as well as the configuration of the positioning element, which parameters may have been determined to maximize efficacy.

Once the system and/or device parameters have been appropriately configured, the target site may be defined, as described in detail below, and then the tMS device 10 may be positioned proximate the treatment site, such as via the manipulation of the positioning element 20. Specifically, the tMS device 20 may be positioned in proximity to one or more of a target and/or treatment site via the manual and/or automated movement of the positioning element 20. For instance, based on previous treatments of this particular subject, or a set of optimal parameters determined based on a plurality of patients previously treated with the same or similar pain experience, treatment site, nerve damage, and the like. Alternatively, the positioning may be determined iteratively, as explained in detail below, such as through a process of steps by which the ideal treatment arrangement for this patient at this time may be determined.

Accordingly, once the target and/or treatment site has been determined, the positioning element may be arranged and/or orientated so as to position the magnetic coil 15 of the tMS device 10 adjacent to a body part that has been identified for treatment, such as in a previous step. In various embodiments, the positioning may be performed by using one or more of the positioning aids described herein. Likewise, once the tMS device 10 is positioned, the treatment session can be started. Before, during, and/or after a treatment session, feedback may be obtained from the patient, such as by eliciting verbal feed back, measuring feedback from the body, determining feedback from one or more of the system components, such as from one or more sensors of the disclosure. Such feed back can be recorded by the system, such as at the control module 70, and can be used to determine optimal administration parameters such as to ensure that the device and/or its components are performing adequately and that the user is experiencing a decrease in pain. In various instances, the feedback may be transmitted to a remote location or stored locally for analysis, and if necessary or otherwise desired, the plan for administration and treatment, and/or the device settings and/or configurations may be adjusted as a result of the feedback and/or its analysis.

In various embodiments, the system may be operated according to one or more of the following steps: The system first may be setup, the various components of the system and system parameters may be arranged and/or otherwise configured, and the functionality of the system and its components may be verified. For instance, prior to or during use of the system, the positioning element 1, such as the robotic system, may be setup, the control parameters and/or the robotic arm positioning may be configured, and the system functionality can be verified by one or more procedures so as to ensure the positioning and administration systems can successfully execute the therapeutic treatments.

In a particular instance, the stimulatory apparatus encasing the magnetic coil, e.g., a butterfly coil, may be moveably attached to the positioning element, such as at or near a proximal end thereof, such as a tool end of a positioning element, such as configured as a robotic arm. Specifically, as can be seen with respect to FIG. 1B, the tMS device may be mounted, e.g., in a precise fashion, to a fixture of the distal portion of one of the segments of the positioning element 20. For instance, the positioning element 20 may have a plurality of segments 20a, 20b, which are configured for being moveably coupled to one another such as via a moveable joint. In some instance, the joint member may include a motor 21a, 21b, 21c, which motor may be configured for enabling movement within the plane and/or for rotational movement. The distal end of the positioning element 20 may include a coupling mechanism, such as an attachment fixture. Particularly, the attachment fixture may be configured for removably coupling to the positioning element 20 with the tMS device 10, such as via any suitable attachment mechanism, such as by bolting directly to the fixture or via an intermediary tool flange, such as where the geometry of the fixture and position of the tMS device 20 in relation to the positioning element 20, e.g., robot, tool end is known.

Once the system is setup, then the target area may be configured and/or aligned. For instance, a target area search sequence may be initiated, and then a target area tracking procedure may begin. Specifically, with respect to system setup, configuration, and functionality one or more marking or signaling indices may be employed, such as one or more passive or active indicating markers, such as a reflective marker and/or a lighting element. As indicated above, a passive or active marker 22 may be removably coupled to any or all of the components of the system, so as to define their position in the defined 3-Dimensional treatment space.

Accordingly, in some embodiments, a marking device, such as a reflective instrument or a lighting element may be attached to one or more of the following areas: on one or more of the segments of the positioning element, such as at the end regions of one or more of the articulating segments, such as at a joint position and/or where an automating element, e.g., a motor unit, is positioned, such as at a base of a robotic arm, at a position proximate to where the robotic arm couples to the tMS device, or at a location positioned somewhere in between. For instance, as can be seen with respect to FIG. 1B, a positioning element 20 of the system 1, configured as a robotic arm, is set forth, where the robotic arm 20 includes a plurality of segments 20*a*, 20*b*, which segments are coupled together at a moveable joint region that allows the two segments to move with respect to one another along one or more planes of motion, and/or may be configured to rotate around an axis defining one or more of those planes.

Also included is a terminal member positioned at a distal portion of the robotic arm 20, to which terminal member the tMS device 10, including the magnetic coil 15, the distance scanner, and/or an imaging element, such as a camera may be attached. For example, an imaging device(s), e.g., camera, may be coupled to one or more components of the system, such as to a housing the tMS device 10, or may be a free standing element 30 that is a separate instrument from the tMS device 10 and positioning element 20. As indicated above, the camera may be a stereoscopic camera that is configured for imaging a three-dimensional space, e.g., of the treatment site, and with the appropriate configurations can image a three-dimensional space of the subject's body, which three-dimensional space defines the treatment site within the body of the subject, thus providing a three-dimensional representation of the treatment site from within the body.

As can be seen with respect to FIG. 1B, the robotic arm 20 includes a marking device 22*a*, in this instance, at the base of the robotic arm, by which the system 1, e.g., via one or more of the imaging component 30 and/or distance scanner 40, can track the movements and positions of the positioning element. In certain instances, the marking device includes a first set of marking elements, such as including a plurality, e.g., 3, three reflective elements. Additional marking devices may also be included such as a primary and a secondary or tertiary reflecting and/or lighting device.

For instance, as depicted here, a plurality, e.g., three, sets of marker devices, 22*a*, 22*b*, 22*c* are useful for defining a three-dimensional space and/or where one or more of the components of the system is positioned within that three-dimensional space, and for tracking movements and orientations of the various elements of the devices, such as with respect to the position of a treatment site of a subject to receive treatment. The geometry of each marker may be uniquely configured so as to function along with the three-dimensional camera system 30 so as to define the three-dimensional treatment space and/or to track the movement of the positioning element 20 within that space. Reflective markers and/or lighting elements or other sensing units may also be used to determine the position and/or orientation of the tMS device 10, e.g., the magnetic coil 15. For instance, the tMS device 10 and/or the positioning element 20 may include one or more sensors that are configured for generating data that may be used for determining the position and/or orientation of one or more segments of the positioning element and/or the tMS device and/or imaging component. Such sensors may include a gyroscope, an accelerometer, a light sensor, a pressure sensor, and the like.

Accordingly, there are a variety of marking devices that may be employed in the system, such as marking devices configured for being coupled to the positioning element 20 and/or tMS device 10, e.g., so as to define the space which the positioning element and/or tMS device occupies, and target site marking devices, which may be configured for defining or otherwise demarcating the site to be treated. Specifically, such treatment area markers may be positioned on the patient so as to define the target area, such as after a suitably configured target search procedure has been completed.

In various embodiments, a calibration procedure may be implemented so as to determine the baseline, e.g., home or at rest, positions of the system components. For instance, a first calibration procedure may be implemented such as a positioning element 20 (e.g., a base and/or segment or joint positioning element) to imaging element 30 calibration procedure may be implemented, so as define the initial position between the positioning element 20, e.g., robotic arm, and the imaging device 30, e.g., camera, such as for the purpose of calibrating the system components. Specifically, each of the positioning element segments and/or joint elements having a marking device positioned thereon may be first placed into their home position, e.g., manually or automatically, such as by initiating a homing sequence program implemented by a local computing resource in communication with the controller of the system components, e.g., via a suitably configured GUI of a display associated with the local computing resource.

Next, the imaging device 30 can be positioned to have the positioning element marker(s) 22*a*, e.g., base marker, in its field of view and within its measurement volume. From this position the rotational angle of the X, Y, and/or Z-axis may be determined, such as by reading the positioning element marker coordinates from the camera in order to correlate the positioning element and imaging device coordinate system.

Further, as discussed above, a distance determining device 40, such as a distance scanner may be included as a component of the system 1, such as where the distance scanner 40 may include a micro distance measurement sensor. In various embodiments, the distance determining device 40 may include one or more laser sensors. For instance, a distance determining device 40, e.g., having a micro distance measurement sensor, may be a free-standing component 40 or may be coupled to one or more other components of the system, such as to a tMS device 10 or an imaging device 30. For example, the distance determining device 40*a*, e.g., the distance scanner, may be removably coupled to the housing of the tMS device 10, and/or may be a plurality of elements that are positioned proximate a magnetic coil 15 of the tMS device, such as between the coils of a butterfly or FIG. 8 coil, or positioned around the circumference of one or more of the coils. Specifically, the distance scanner 40 may be attached to the housing of the tMS device 10, such as to be attached in a position that is proximate to the butterfly coil, so as to be able to determine one or more of the distance of the coil from the target site and/or body of the subject to be treated, and/or to be able to determine the orientation of the magnetic coil 15 and/or the tMS device 10.

Figure 2A:
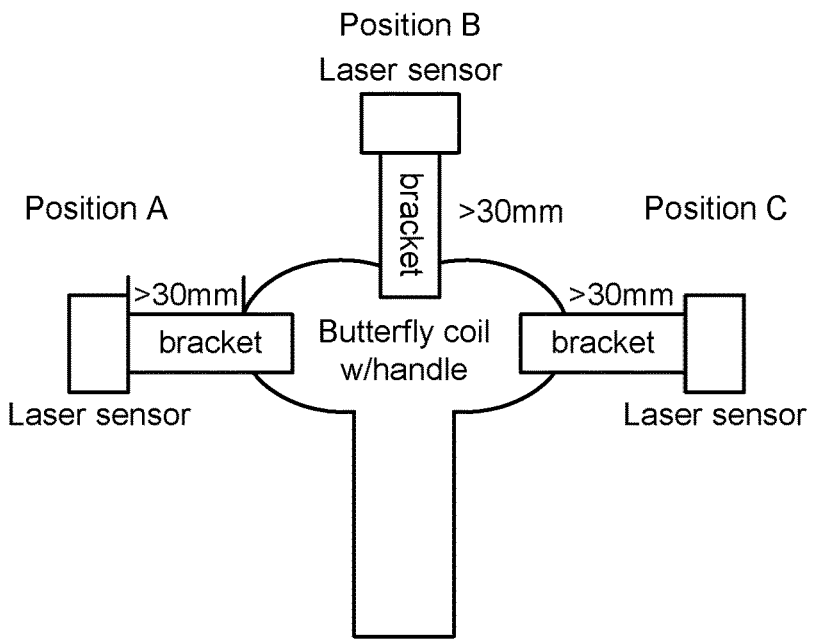
FIG. 2A provides an illustration of an exemplary tMS device having a distance measuring device associated therewith.

As can be seen with reference to FIG. 2A, the distance scanner 40*a* can be positioned at a known, precise location, such as by using a bracket coupling mechanism, an adhesive, or other suitable coupling mechanism. Particularly, distance scanner 40a, or other distance determining sensor, can be mounted closer or further from the tMS device 10 and magnetic coil 15, such as from about 1 to about 5 mm, from about 6 to about 15 mm, or more than about 16 to about 30 mm to about 40 or to about 50 mm away from the coil 15, such as to eliminate malfunction of the sensor due to magnetic field interference, or alternatively the sensor may be insulated to prevent such interference. Where an attachment member is employed as a coupling device, such as a bracket, the various members of the coupling device can be substantially identical so as to allow for easy calibration/integration into the system.

Figure 2B:
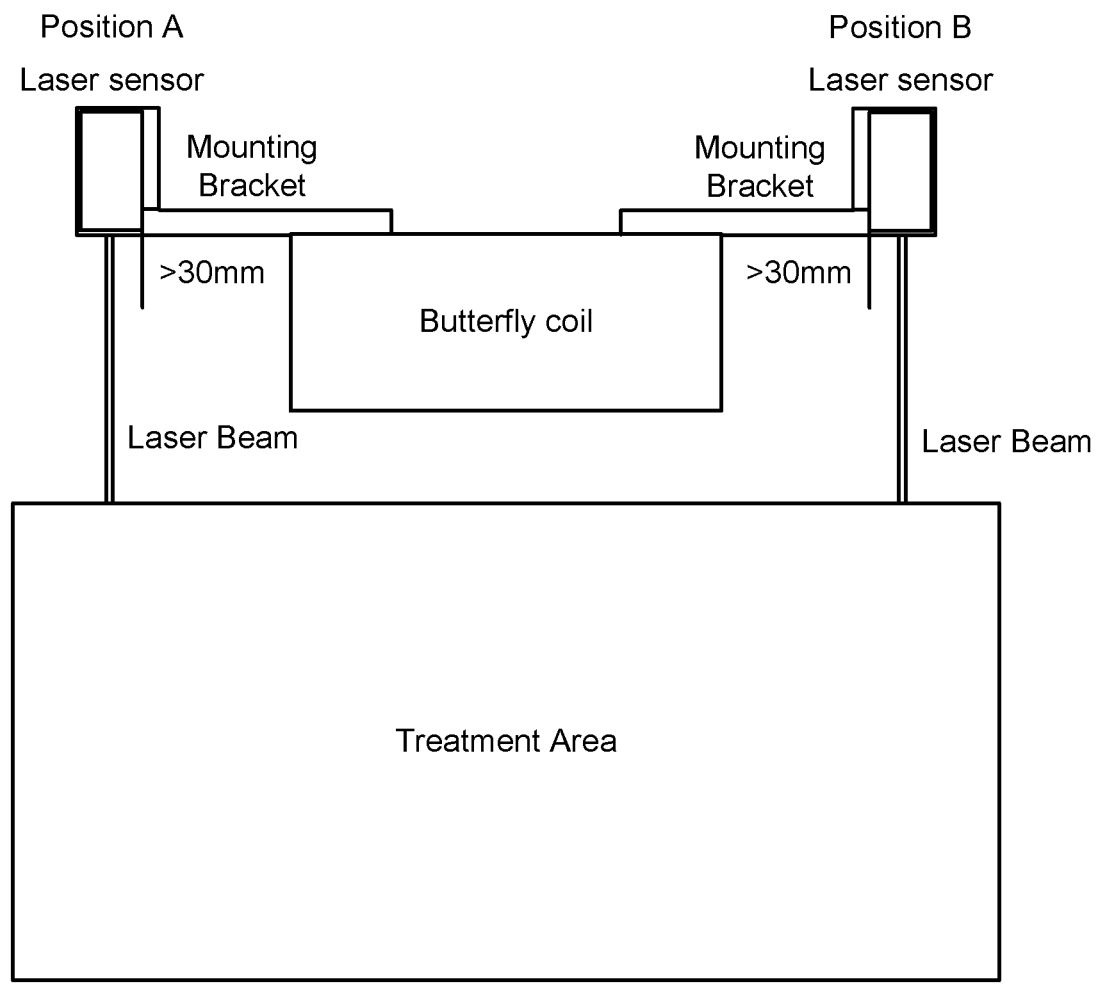
FIG. 2B provides an exemplary embodiment of the tMS device being positioned in proximity to a target area.

More particularly, the distance determining device 40, e.g., scanner, can be mounted or otherwise coupled to the housing of the tMS device 10 in a variety of positions as set forth in FIGS. 2A and 2B. For instance, as can be seen with reference to FIG. 2A, the scanner and/or sensor 40a may be positioned at Position A, B and/or C, such as depending on the location and/or configuration of the treatment area, such as depending on a location determined to allow the sensor(s) to generate the most comprehensive and accurate position and orientation data for the tMS device 10 with respect to the target and/or treatment sites demarcated on the subject to be treated. For example, the tMS device 10 may include a single distance scanner 40a that is positioned around a circumference of the tMS device, e.g., as exemplified by positions A, B, or C, (or any position in between), or a plurality of distance scanners may be included and positioned in multiple locations, 2, 3, 4, 5, etc. around the circumference of the tMS device housing. Additionally, although illustrated being attached to the tMS device via a bracket, in various embodiments the distance scanner can be attached directly to the tMS device, and in various embodiments, a distance scanner can be positioned between two magnetic coils or around a circumference of one or more of the magnetic coils. Further, as illustrated in FIG. 2B, the distance scanner 40, e.g., including a laser sensor, may be mounted to the tMS device housing, such as by an intermediate mounting bracket, in a manner so that the sensor is positioned a given distance from the housing and/or a boundary of the magnetic coil, in this instance, 30 mm from the housing.

The distance determining device 40 may include a communications and/or a source of power, e.g., a rechargeable battery or other energy reserve, and as such the distance scanner, or any other component of the system, may be configured for wired or wireless power supply and/or recharging, e.g., of an included battery, and/or for wired or wireless communications. For example, the sensor device may be electrically and communicably connected, e.g., in a wired configuration, to the tMS device and/or positioning element, such as via an I/O connector. In such an instance, this wired connection may provide 24 VDC power to the sensor module and may use analog input to read in distance measurement values. In other embodiments, digital distance measurement data may be generated and communicated digitally, such as via one or more wireless communication mechanisms as discussed herein.

Figure 3:
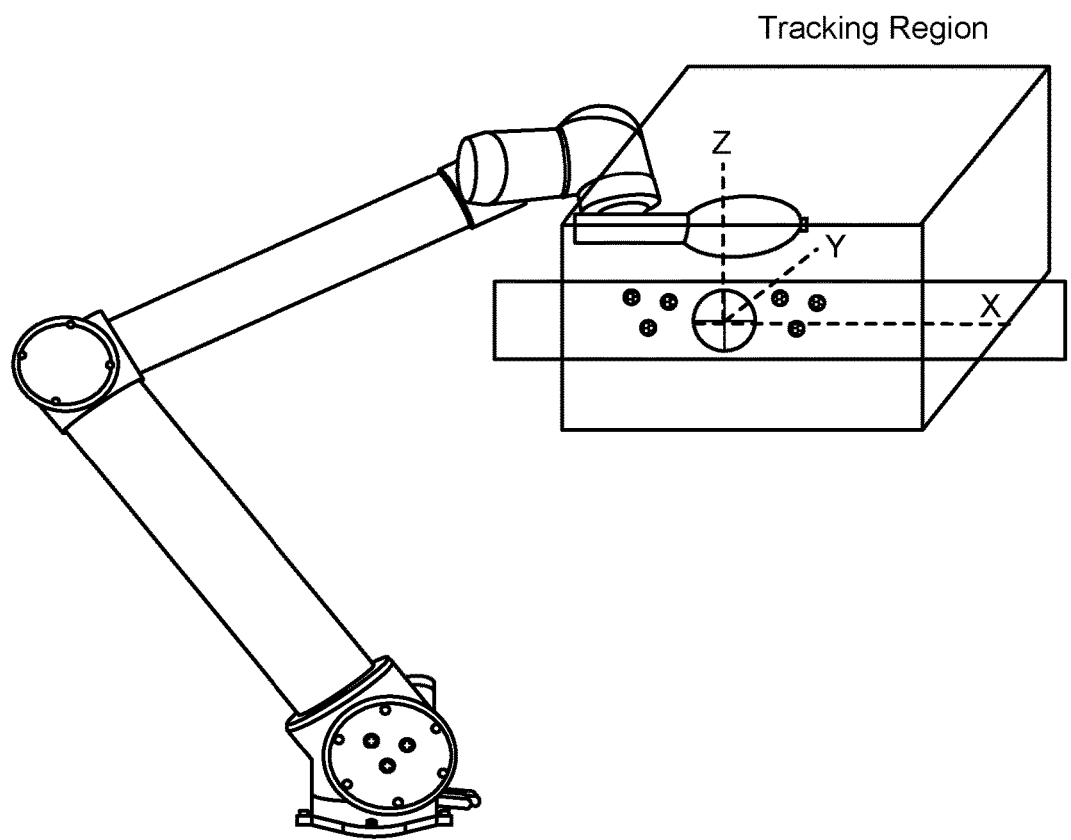
FIG. 3 provides an illustrative embodiment of the system determining the position of a positioning element and tMS device within a 3-D space in accordance with the teachings of the disclosure.

Together the distance determining device 40 and/or the image capturing device 30 may be employed to track the movements and positioning of the positioning element 20. For instance, the imaging capturing device 30 may be used to define a three-dimensional space within which the positioning element 20 operates, and the distance determining device 40a, 40b may be employed so as to determine the position and/or the orientation of the tMS device 10 and/or magnetic coil 15 thereof, as depicted in FIG. 3. In such an instance, the system itself, such as via a suitably configured A/I module of the system, may be employed to determine the space and optimal positioning of the system components within that space, such as relative to the target site (see FIG. 4), for the effective delivery, from the magnetic coil 15, of a magnetic field sufficient to treat a subject suffering pain at the treatment site.

In other instances, this configuration and orientation may be determined co-operatively or manually, such as via the input of an operator, clinician, or other system and/or device operator. For example, the clinician/operator may enter various distance values, such as a minimum or maximum distance value, e.g., for all coordinate dimensions of the treatment space, so as to define the tracking region for the positioning element and/or the tMS device. Hence, this dimensionality, e.g., the minimum/maximum distance value, may be applied to each direction X, Y, and Z, so as to from a digital, e.g., mathematical, representation of the three-dimensional treatment space within which the components function, such as to track the movement of those components through the treatment space. Specifically, the minimum and/or maximum distances, e.g., in mms or nms, can be determined and specified from any origin, but typically will be defined with its center being the center of the target area and/or treatment space. More specifically, one or more, e.g., all, of the markers within the tracking region and/or treatment space may be characterized and defined, and then the boundaries of a treatment site, and a tracking region within that treatment space, may be determined so that the movements of the various components of the system may be within the allowable measurement volume of the imaging device(s), e.g., during all times of therapy. It is useful for the tracking region to be within the workspace of the positioning element.

Particularly, as can be seen with respect to FIG. 3, during therapy, the positioning element 20 will move the tMS device 10 so as to position the tMS device 10 so that it is proximate the determined treatment site, and once there, may make adjustments to the position and/or orientation of the coil 15, such as by tracking the of one or more of the position marking devices 22, such as one or more marking devices 22a on the positioning element, at the treatment area, and/or a marker on the tMS device, so as to determine their coordinates in the treatment area, and to determine and assign distance measurement as well as coordinate values to each component of the system 1. For instance, position adjustments may be executed within the defined treatment space, such as within a determined tracking region within that space. In various instances, a potential movement outside of the defined region and/or treatment area may be prohibited by the system, either mechanically or electronically. More particularly, if a target area tracking results in adjustments outside the tracking region the positioning element, e.g., a robotic arm, will stop movements at the boundary of the tracking region and/or treatment space.

Accordingly, the system 1 may be configured for tracking the movements of the positioning element 20 within a defined space and relative to the subject. For instance, the 3-D space may be configured for determining and defining the boundaries of the 3-D space, and further defining the tracking region within that space. Particularly, as indicated, one or more segments of the positioning element 20 may include a reflective marking instrument 22, and/or the image capturing device 30, e.g., 3-D camera, may also include a reflective marking instrument or other sensor 40b, e.g., position determining sensor, such that movements of the positioning element 20 relative to the movements of the camera 30, if any, can be determined and tracked. In certain instances, the marking instruments may include one or more sensors that are in communication with one another, so as to communicate relative positioning one to the other. Particularly, the 3-D camera 30 may have a sensor 40b that is capable of communicating with the sensor 40b, e.g., marking device on the positioning element. In such an instance, the 3-D camera position sensor may be configured and positioned so that the various marking devices, e.g., on the positioning element and/or on the patient, at the target site, are within the defined treatment region, e.g., during operation of the tMS device 10, such as during target area tracking.

Specifically, prior to the initiation of treatment, and after defining the treatment region, verification of system functionality may be conducted. For example, the system control can verify the following: That the positioning element and control module are powered on and ready for use. The image capturing device is powered on and ready for use. The distance determining module, e.g., containing a laser distance measurement sensor, is powered on and ready to use. And the tMS device and magnetic induction element are powered on and ready for use.

Once the system is appropriately configured and its components set up and powered on, a target area alignment procedure may be implemented. In such an instance, a device operator, such as a clinician, may manipulate one or both of the positioning element and the attached tMS device, including the butterfly magnetic coil to the desired target area, such as manually, when the positioning element, such as a robotic arm, is in free-drive mode. However, in various instances, the system may be configured for moving the various components thereof automatically and/or autonomously, such as by the control unit of the system, in conjunction with the imaging component, driving the motors of the positioning element and/or tMS device into the appropriate positioning. In particular embodiments, this may be accomplished further in conjunction with a suitably trainer artificial intelligence unit and/or virtual reality element of the system.

Figure 4:
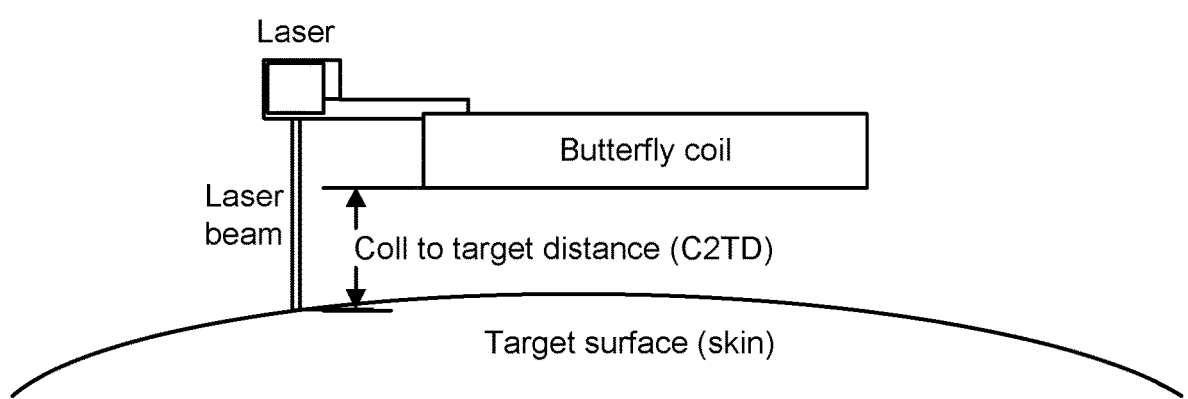
FIG. 4 provides an illustrative embodiment of a method for determining the distance between a magnetic coil of a tMS device from a target area on a subject to be treated.
Figure 6A:
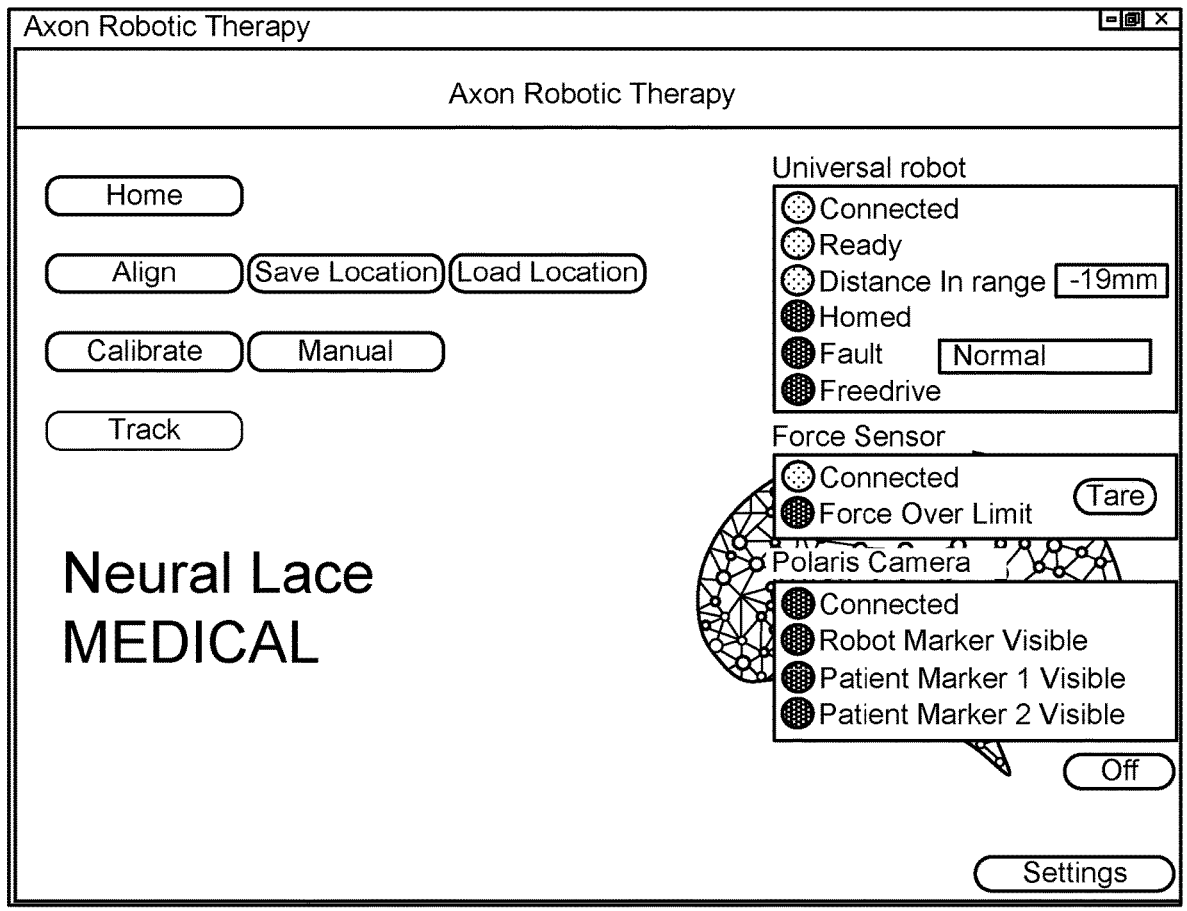
FIG. 6A provides a representation of a graphical user interface (GUI) for use in configuring the system.
Figure 6B:
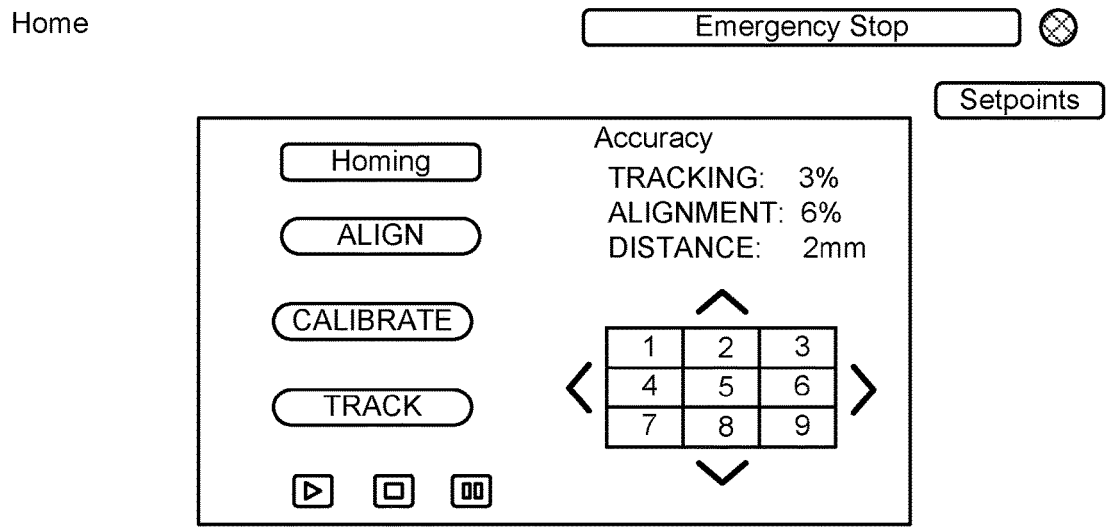
FIG. 6B provides a representation of a GUI for selecting a procedure to be implemented by the system.

As depicted in FIGS. 4 and 6B, to aid in this positioning, the system may generate a distance measurement display that is configured to show the coordinates of one or more of the segments of the positioning element and/or the tMS device within a defined treatment space, and/or with respect to a measured distance from a treatment site. For instance, the system may include a graphical user interface that is configured for being presented at a display of the system, such as a display associated with a computing unit 70, where the graphical user interface displays one or more distance measurement values, such as obtained from one or more of the distance sensor and/or imaging component, and which can be used, either by the system or manually, as a guide for positioning and alignment. In various instances, this may be used, such as by the clinician, in manually positioning the positioning element 20 and/or the tMS device 10.

For example, various of the components of the system may include one or more distance scanning lasers 40 that are positioned so as to determine where any given element is positioned within a defined space and/or with reference to a target area, such as adjacent to a treatment site. The sensors can communicate amongst themselves, one or more of the controllers, and/or the imaging component so that the movement and orientation of the various components of the system may be tracked, such as in relation to a coordinate system, defining positions and distances, e.g., in three-dimensional space, and/or can be used to build a virtual space electronically that can be digitally represented at the GUI of the system, within which the various components of the system may further be digitally represented and their movements controlled and/or traced within the virtual space. In various embodiments, the system can use the virtual space to automatically move the system components to the determined treatment site at the generated optimal distances.

Accordingly, in various instances, the various components of the system may include multiple distance scanners, e.g., lasers, that measures distance changes over a defined space so as to determine how far a first part of the system component is from one part of the target site, and further how far a second part of the system component is from a second part of the target site, e.g., on the body of the patient, such as where the body part to be treated is curved, such that positioning element and tMS device can be positioned to accommodate supply treatments to the body part while yet accommodating different body topologies. In various embodiments, the housing and components of the tMS device 10, including the magnetic coil 15 therein, is configured for being configurable, such as where the right hand side of the tMS device, e.g., the RH coil, is configured to be moved and orientated with respect to the left hand side of the tMS device, and vice versa. Once the positioning element 20 and the tMS device 10, including the magnetic coil 15, has been grossly positioned within the target area, near the target site, then a fine motor movement protocol can be initiated so as to finely move the positioning element and for orientating the tMS device 10 so as to be in a close position to the target site, such as for effective and efficient delivery of treatments, e.g., magnetic fluxes, to the site of treatment.

Accordingly, once moved generally to the target area so that the device is within the desired location, then the clinician or other operator can start the target area detection and fine-tuned alignment sequence, and the refined treatment area alignment can be defined. The treatment area alignment may define the work plane the device will move in during the target area detection sequence and tracking.

For instance, as set forth in FIG. 4, a target area and treatment site detection sequence is provided. When initiated, the target and/or treatment area detection sequence will either automatically move or direct the clinician in moving, such as via providing an indicating feedback, e.g., visually, vibratory, tonally, or the like to the clinician while manually moving the components, such that the coil is moved along the work plane, such as in a predetermined grid pattern, to precisely determine the target area and define one or more particular treatment sites. Particularly, the tMS device 10 may be powered on along with one or more associated distance measuring scanners 40, and may be orientated toward the target area such that distance measurements from one or more portions of the tMS device housing and/or coils 15 is taken with respect to the body to be treated, such as within the target area.

More particularly, a generalized optimal target distance may be generated beforehand, which may then be entered into the system so as to define a general target area, within which target area a more refined treatment site may be defined. Hence, the system itself or a clinician or other operator of the system may then determine one or more coil to target distances. In one embodiment, the system or the clinician can determine and specify a first coil to target distance value, which may then be used by the system to define a target area parameter, which may then be presented for observation on the GUI. During the target area and/or treatment area detection and target tracking procedure, the general position of one or more of the positioning 20 and/or tMS device 10 may be maintained, and the distance between the bottom of the tMS device housing and/or individual coils 15 and the target area, e.g., using a feedback signal from the distance sensor 40, may be determined and a treatment area defined thereby.

A tMS device and/or coil to target site distance tracking and/or coil alignment may be performed, such as where the tMS device and/or coil to target site distance may be defined. This may be done in a manner that the distance between the bottom of the coil and the point where the distance scanner detects the skin within the treatment area is defined. This general procedure is exemplified in FIG. 4, where the tMS device 10 including a distance scanner 40a, e.g., a laser, is positioned above the skin near a target area, at a first determined distance away from the skin, such as where the distance is defined by the distance measured between the target skin surface and the bottom of the tMS device and/or coil. The device 10 may then be moved across a selected area so as to define a particular target site.

Accordingly, once the target area has been more precisely defined, then the target site can be determined, and from that target site, a first treatment area may be determined, and finally, one or more treatment sites may be defined. During a treatment area search and target tracking procedure the tMS device and/or coil may be adjusted, e.g., in the X, Y, and Z directions, to track the treatment area and maintain desired distance, and once the target site is defined, then a treatment area may be determined, and/or a treatment site derived thereby. In such instances, the device components may be manipulated within the treatment area so as to determine not only the appropriate treatment distance, but also the treatment orientation of the device, and in order to do this, the tMS device and/or positioning element may be moved and/or rotated about the X, Y, and Z planes and/or axes so as to appropriately orientate the magnetic coil to the treatment site for the delivery of treatment. Accordingly, once the target area has been bounded and a target site identified and defined, then a treatment area may be defined, form which a treatment site may be determined, such as in a grid search type sequence.

Specifically, as set forth in FIGS. 5A-5D, a grid-type search sequence may be implemented. For instance, starting with the outer bounds of a determined target area, a grid area representing the target site may be defined. The grid may include a plurality of rows and columns offset from one another so as to define a set of boxes having a determined area. Any number of columns and any number of rows may be used to define any number of boxes, such as where the boxes are dimensioned so as to define target site, which target site can define the area wherein a subject is experiencing pain to be treated. However, for the ease of use the rows and columns define a grid, such as a grid of squares, where each square is made up of sides having substantially equal lengths. These lengths may be of any length from nm to mm to cm and/or to inches, feet, and meters, etc. depending on the type of pain and the area affected.

Nonetheless, in various instances, the grid includes three columns and three rows together which form a larger box, but any number of columns and rows may be employed such as 2, 4, 5, 6, and the like. In particular instances, each side of each box will have a length of about 1 to 5 to about 10 nm to about 1 mm to about 10 mm to about 1 cm to about 10 cm or more. As depicted the length and width of each box is 3 mm, which means that the collection of boxes has a length of 9 mm and a width of 9 mm. As indicated, this overall box forms a search grid within which the positioning element and/or tMS device may be finely moved and operated in a manner so as to define a treatment area, wherefrom within the treatment area, a more finely defined treatment site may be determined.

Figure 5A:
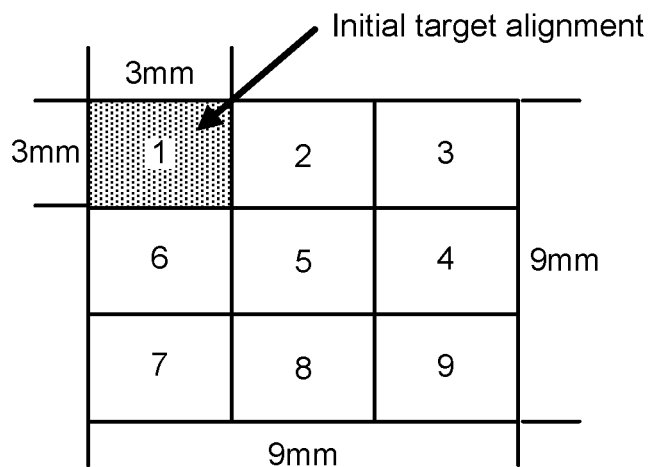
FIG. 5A provides a virtual grid-matrix for use in determining a target area for the application of a targeting protocol.

For instance, as depicted in FIG. 5A, a representation of a grid, having a box-like configuration is presented. In this instance, the grid includes 3-rows and 3-columns which make up a total of 9 boxes, which 9 boxes together define the target area. As represented, each box has a length and a width of 3 mm, this defines 9 different areas, 1-9, which can then be tested, iteratively, to determine whether and/or to what extent a nerve underlying the target area is reactive to a treatment applied by the system herein to the skin of the subject, such as the skin represented by one or more of boxes 1-9.

Hence, for the purposes of defining a target area from which a target sight may be defined, and once defined a treatment area, from which a treatment site may be determined, the tMS device and/or positioning element may be moved in accordance with a defined grid-like pattern, such as sequentially from areas 1 to 9, so as to determine the bounds of the area(s) to be treated. Accordingly, a grid search sequence can be initiated, such as starting from an initial area, e.g., box 1 in the target grid, whereby the area represented by box 1 can be tested to determine if any nerve cells within that area are reactive to the application of the therapy. Specifically, the positioning element may be moved and/or otherwise manipulated so as to align generally with the area represented by box 1, and once aligned therewith, the device may be operated in a manner so as to test area 1 in order to determine the level of reactivity, with respect to pain remediation, that results from applying an initial treatment to the area.

If the area is to some extent reactive, e.g., the subject experiences a decrease in the feelings of pain when a magnetic flux is applied to the area, then this may be indicative that the pain causing nerve may be positioned internally at least within this area. In such an instance, the area represented by box 1 may then be demarcated for further testing to determine if that area should be included in an initial treatment area. For instance, if a magnetic flux is generated and targeted at the skin area represented by box 1 aligns with a configuration of the nerve causing the pain, e.g., in such a manner as to activate the nerve fiber, an amelioration or at least a diminution in pain will be experienced. This diminution of pain, therefore, would identify area 1 as being part of the locus of pain that defines the treatment area. However, if the nerve causing the pain is not significantly projected in this area, then the magnetic stimulation will have no effect on the nerve and there will be no concomitant diminution of pain. Thus, area 1 may then be excluded from the to be determined treatment area.

Once box 1, representing a first area, has been tested, from there the device may be moved to align with the area represented by box 2, and area two may then be tested. This process may then be repeated so as by moving from one area to another incrementally, in any logical (or random) order so as to test each area represented by the grid-like structure. For instance, each box may be tested such by moving the positioning element and/or tMS device, such as in planar and/or rotational movement with respect to the skin of the target area. Once so aligned, then the tMS device may be operated so as to generate and direct a magnetic flux toward the targeted area, e.g., with a given wave characteristic expected or known to be able to generate a response in a sensitive nerve fiber.

If the area tested is sensitive to the treatment, signified by pain diminution, then it can be demarcated so as to be included in an initial treatment area, whereas if the area is not sensitive to the treatment, then the area can be excluded from the to be defined treatment area. The treatment area, therefore, can be defined by selecting the boxes representing areas in the grid that have proven to be sensitive or otherwise reactive to the inductive magnetic field, which areas, thereby, define the configuration of the underlying nerve to be treated. In various instances, once the treatment area has been defined, this area can be further tested so as to confirm the presence of the underlying nerve to be targeted, such as by performing an intra-tissue imaging procedure, such as MRI, fMRI, etc.

Accordingly, in various embodiments, in testing the grid-like target area to define the configuration of the treatment area (and/or underlying nerve to be treated), one or more target areas may be tested, as described herein, and when identified as being reactive to the treatments, then the box demarcating that area may then be included for further testing. In this manner, the boxes to be included for further testing may collectively form a given configuration, such as a configuration that includes a plurality of boxes. Specifically, a collection of reactive boxes may form a pattern, such a vertical or horizontal or diagonal row-like pattern. Particularly, this pattern may be indicative as to how the underlying pain causing nerve is configured, such as if its fibers are aligned horizontally, vertically, or diagonally. Other configurations may also be present, such as where the boxes show a branched configuration, such as where boxes 1, 3, 5, and 8 are implicated as being sensitive to the treatment administrations. Of course, other patterns can be evidenced based on the branching of the nerve tissue.

Therefore, in determining one or more of a target or treatment area, the system devices, e.g., the positioning element and/or tMS device, may be moved, e.g., incrementally and/or sequentially, so as to test the entire target area, such as in a grid-like pattern, in a manner to determine one or more target sites to be further tested. For instance, as represented in FIG. 5A, a first pass of analysis may be performed by the system so as to determine the range of the target area, such as defined by a grid of boxes representing areas 1-9, where the target area can be configured to cover a 9 mm×9 mm section, such as where each box is 3 mm in length and width. In such an instance, an initial starting area may be selected, e.g., from boxes 1-9, and the positioning element and/or tMS device may be moved from box to box in such a manner as to position the tMS device proximate the box representing the pre-defined skin area to be tested. A test signal, e.g. burst of magnetic flux, can be applied, and a response may be evoked in the body and evaluated with respect to its level of reactivity. If reactivity is detected, then the box representing the area of reactivity can be demarcated as a treatment area that can be subjected for further testing.

Figure 5B:
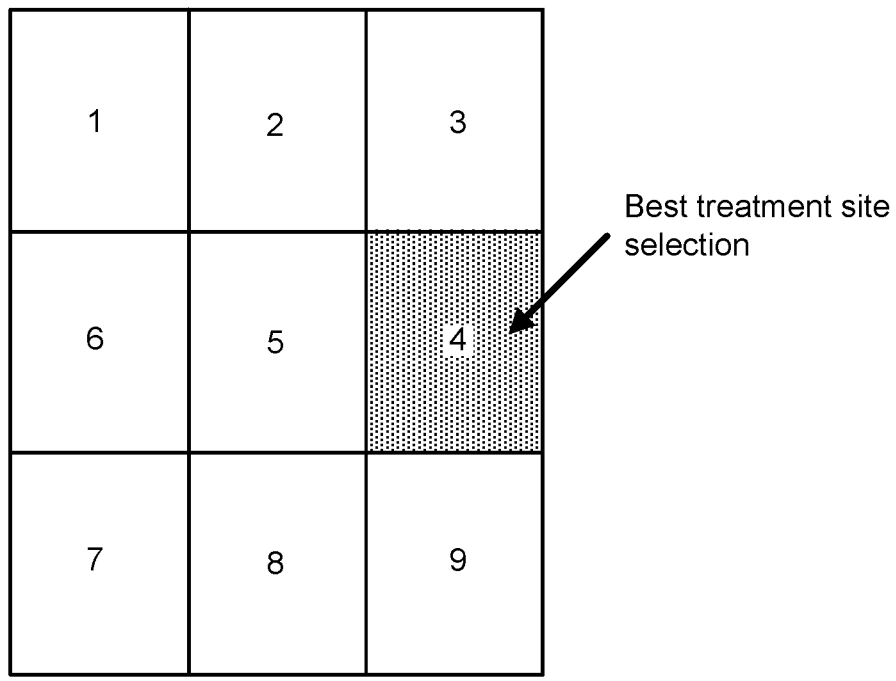
FIG. 5B provides a virtual grid-matrix for use in determining a target site for the application of a targeting protocol.

Accordingly, in this manner, a sequential positioning and testing can take place where the testing follows a specified grid-like pattern, for the purpose of determining one or more treatment areas, from which area, one or more treatment sites is determined. For instance, as depicted in FIG. 5B, through the iterative process of positioning the tMS device to deliver a magnetic pulse to each target site within the target region, and determining the reactivity of one or more underlying nerves therein, one or more treatment regions, in this instance area 4, can be selected for further testing, so as to determine one or more precise treatment sites, such as by subjecting the determine treatment area, e.g., area 4, to a second pass of the system.

For example, one or more passes, such as both a first, a second, and/or a third pass, may be initiated and implemented through interfacing with the system GUI, through which GUI the various dimensionalities of the grids may be determined. Specifically, as seen in FIG. 6A, a first user interface, e.g., a start screen, can be provided where a user can access and configure the system for use. The system, therefore, may have a plurality of modes of operation from which the user may select: including the running of an alignment or calibration operation, selecting a manual or automatic operation mode, for saving the configurations for a given position or location of targeting or treatment, and/or for loading a previous saved positional configuration. A status of operation may also be indicated from this screen, such as for indicating the status of connectivity and/or readiness for use, e.g., for the positioning element 20 and/or the tMS device 10 and/or distance scanner 40 and/or force-torque sensor, and the like, to determine if the various system components are ready for use, in use, in the home position or targeted position, or if the positioning element in in free-drive mode. A fault level and present coordinates, including distance range, may also be shown.

A status indicator for the force-torque, or other pressure sensor, may also be included, such as for showing the status of connectivity, the set-point for the sensor, and/or if the limit has been exceeded. Likewise, a status indicator for the imaging element, e.g., a camera, of the system may also be presented, which status indicator can include a status of connectivity, e.g., of the camera to the system, the connectivity of the camera to one or more of the electronic and/or reflective marking devices, and/or whether they are in view of the camera. If such connectivity fails, the system may automatically seek to reconfigure itself to re-gain connectivity, or may signal an alarm so as to allow an operator of the system to manually reconfigure the system components so that they are in an appropriate working configuration.

FIG. 6B depicts a home screen of a user interface, which home screen can be accessed by interfacing with the start screen, wherein the home screen presents a list of operations that can be selected to be run by the system, such as a homing, aligning, calibrating, and/or tracking operation may be selected to be run. A set-point screen can also be accessed via the home screen, whereby the various set points of the system can be set. The current system status may also be presented, such as where the current accuracy is set forth, the tracking rating and alignment can be demarcated, and/or the current distance between the target and/or treatment sites and the positioning element and/or tMS device may also be displayed. Control features may also be presented such as a virtual start, stop, and/or a pause button, such as for controlling the operations of the system. An emergency stop and/or withdraw button may also be presented, which emergency stop button may be used to stop system functioning and/or return the positioning element to the retracted, home position. A targeting and/or treatment matrix, e.g., grid, may also be presented, whereby the present sector being or to be targeted and/or treated may be presented and/or indicated on the home screen, or the actual tracking grid can be accessed. This grid may simply indicate the current tracking and/or aligning status of the system with respect to the targeting and/or treatment area, or the grid may be configured for allowing the operator to manually enter the area to be targeted and/or treated, such by clicking on the demarcated area, as explained in greater detail below.

FIG. 6C depicts a set-point screen, such as may be accessed via the home screen. The set-point screen may present various different system parameters that can be set so as to appropriately configure the system. For instance, the set-point screen may present a tracking and/or treatment region set point, such as for setting a dimension for an area within which the treatment is to be performed, and/or may include a coil to target distance set point, such as for setting a distance of the tMS device, e.g., magnetic coil, to the area to be treated. Other set point factors may also be presented such as for determining the dimensions of a targeting and/or treatment area, such as within which one or more targeting and/or treatment protocols may be implemented, such as to finely define the treatment site.

For instance, as explained herein, the positioning element may be moved in three-dimensional space within an area of treatment, such as an area within which the movements of the device and subject of treatment may be tracked. Hence, this space may be defined by the subject to be treated and the devices of the system. Particularly, by entering the dimensionality of the tracking and/or treatment space, therefore, the operator can define the treatment area, specifically, the minimum and/or maximum distances the positioning element and/or tMS device can move within the treatment space. Likewise, as discussed, once a treatment area has been determined, then the treatment site may be determined through an iterative process of experimentation, so as to define the region of greatest reactivity to treatments. In performing this function, therefore, one or more grid-like areas may be defined, and used as potential sites for the application of one or more treatments.

Accordingly, the set-point page may include one or more additional parameters for defining one or more grids, which grid may be used to determine the targeting area, e.g., by use of a first grid, and once the targeting area has been determined, this area may be used to determine treatment area by which determination, e.g., by use of a second grid, one or more treatment sites may be defined. Additionally, a calibration and/or treatment time can also be set, such as to define the time period the tMS device will apply a magnetic pulse to a target and/or treatment region, such as to calibrate the device and/or treatment methodology.

Figure 6D:
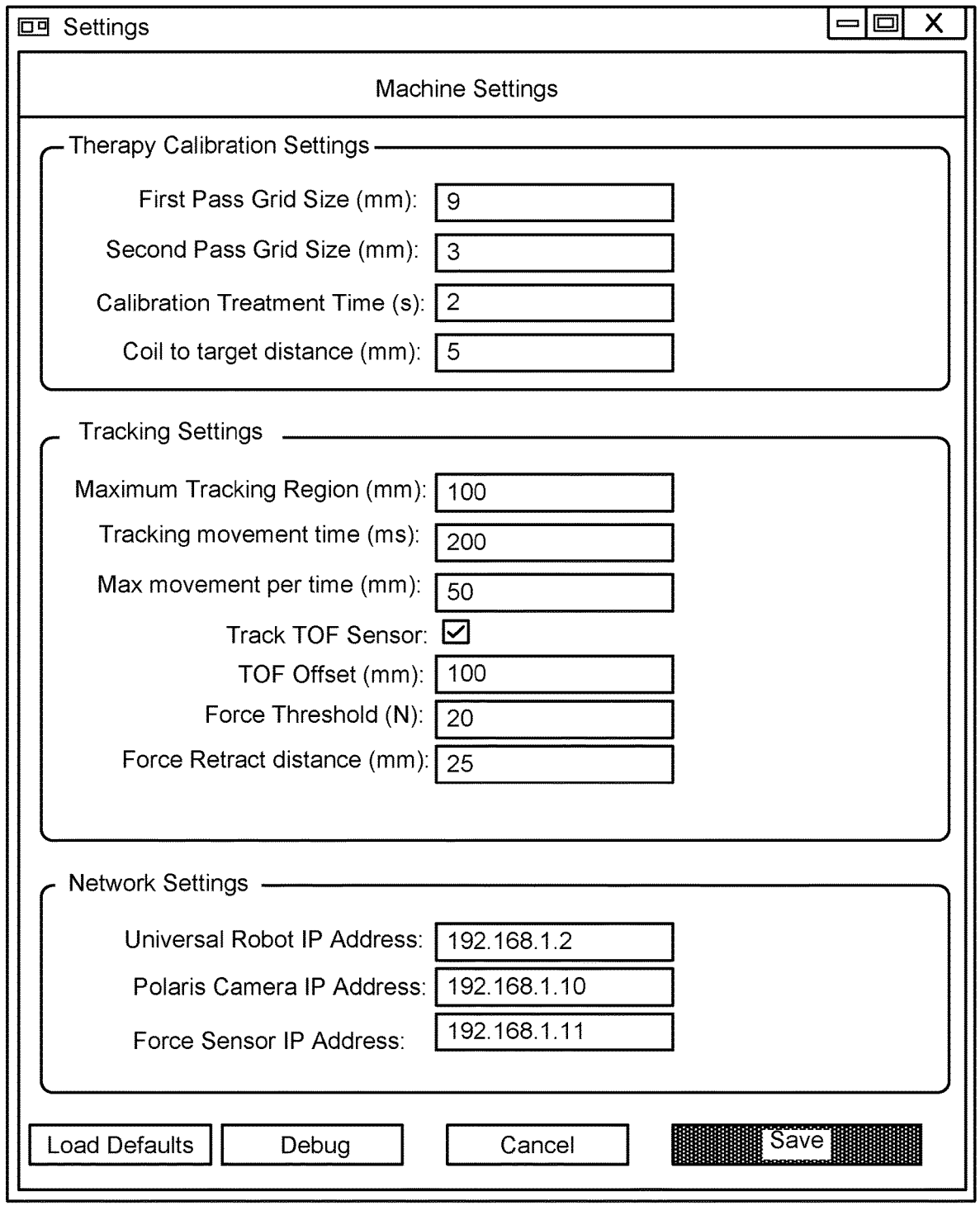
FIG. 6D provides a GUI for displaying data pertaining to a status of the system.

As can be seen with respect to FIG. 6D, both the first grid, e.g., used to define the target area, and the second grid, e.g., used to define the treatment area, may have a dimensionality that may be adjustably selected at the GUI. Particularly, an operator of the system can initiate a first pass target and/or calibration selection protocol from the GUI, which will then start a first pass of testing, as exemplified in FIGS. 5A and 5B, so as to determine the best target site selections. Calibration treatment times and target coil distances may also be adjustably selected. As indicated, in this instance, the grid may first be composed of relatively larger boxes having lengths and widths of about 3 mm, 4 mm, 5 mm, 6 mm, 10 mm, 20 mm, and the like. So as to determine potential target sites.

Figure 5C:
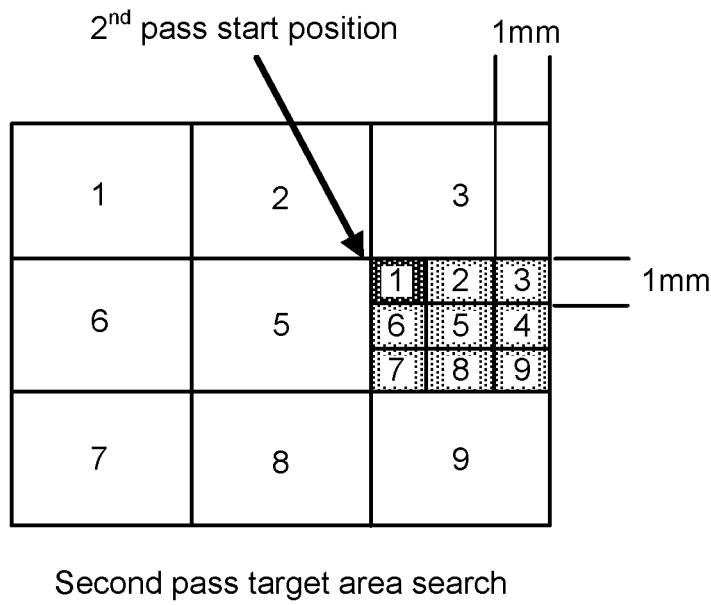
FIG. 5C provides a virtual grid-matrix for use in determining a treatment area for the application of a treatment site determination.
Figure 5D:
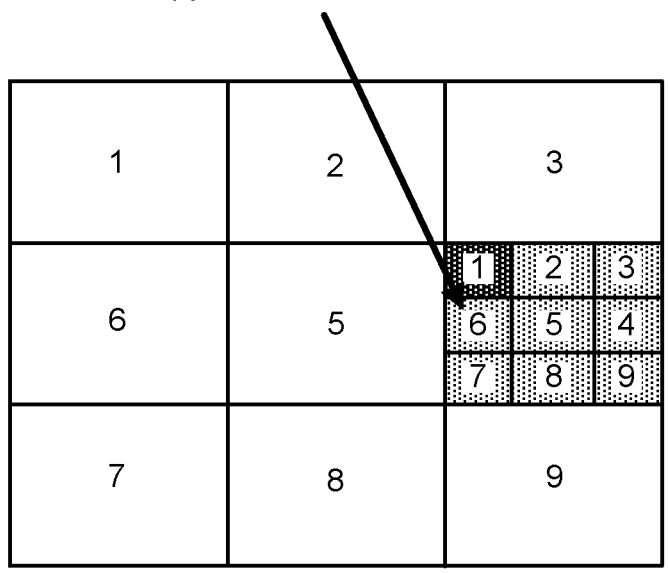
FIG. 5D provides a virtual grid matrix for use in determining a treatment site for the application of treatment.

Then, as depicted in FIG. 5C, one or more targeted sites may be selected for further targeting analysis, where the selected target site now forms a treatment area, which itself may form a grid where each box has an area of 1 mm×1 mm. Hence, upon the operator's selection of the best, e.g., most reactive, target sites, in this instance area 4, the selected target site may then be separated into a sub-grid representing, in this instance, 1-9 different potential treatment areas. Consequently, as depicted in FIGS. 5C and 5D, once the secondary grid, e.g., sub-grid, has been selected and formatted, the targeting sequence can be repeated, such as by repositioning the tMS device to a new start position for the second pass and restarting the sequence in the selected target site, e.g., 1, and progressing the device through the newly defined treatment areas 1-9, so as to better determine one or more particular treatment sites, e.g., treatment site 6, which site, once identified, can be selected as one or more therapy treatment sites.

For instance, as discussed above, during these procedures, the positioning element, such as the robotic arm and/or the tMS device, can be moved manually by the operator, or automatically by the system, such as based on one or more predetermined parameters, such as where the system determines the parameters to be implemented in accordance with the various calculations that are employed to determine the optimal device positioning, orientation, treatment parameters, and/or configurations. In various instances, the GUI may present an interactive interface, e.g., including toggles, that may be manipulated by the operator to move the positioning element and/or tMS device. For instance, a set of X, Y, and Z toggles may be presented for moving the positioning element and/or tMS device sideways in a horizontal direction, upwards and downwards in a vertical direction, and diagonally, respectively. Toggles for rotating the components of the system, e.g., about an X, Y, and Z axis, may also be provided.

Accordingly, once a first pass has been performed, e.g., manually or automatically, then a second pass may be performed, such as where the positioning element and/or tMS device, including the magnetic induction element, may be moved into a starting position, such as at one grid location, e.g., represented by area 1 of FIG. 4, and then a new targeting procedure may be implemented, as per above, where the positioning element and/or tMS device is moved from one location, e.g., 1, to another, e.g., sequentially, so as to determine the appropriate treatment areas, from which one or more treatment sites may be determined.

Once this second pass has been performed, the operator or work flow management system, e.g., controller, can then initiate treatments at the selected treatment site, such as by selecting the starting area for initial therapeutic delivery of the magnetic pulse. In this manner, the positioning element may manually or automatically move the coil to the treatment starting position, and once the treatment region has been defined, one or more treatment markers, e.g., reflective or lighting elements, may be positioned proximate the determined treatment sites, and treatment may be delivered to the selected areas composing the individual treatment sites.

At any time, but particularly after the target area has been defined, a calibration protocol can be initiated, whereby the distance, time, duration, frequency, pulse intensity, amplitude, wavelength, and/or other device and treatment parameters may be determined. Any one of these dimensionalities can be selected and modulated such as at a system interface presented at a display associated with the control unit, e.g., stand alone computer, of the system. For instance, as set forth at FIG. 6D, the system may include programming that is configured for generating a graphical user interface (GUI), such as for selecting and setting the various system parameters, and or for running one or more treatment protocols and/or a positioning sequence and/or calibration process.

Specifically, in a first instance, the dimensionality of a first and a second grid area may be defined, see FIG. 6C, such as by entering at the GUI interface a desired length and/or width of the target area, so as to define an initial target area, from which the dimensionality of a second grid area, e.g., a treatment area, may then be defined. Further, the characteristics of the positioning procedure and/or a calibration process may be selected from the GUI. For example, an initial general magnetic flux, e.g., treatment, application time and/or coil to target distance can be selected or otherwise entered into the system, whereby the initial distance that the positioning element may hold the tMS device, and/or magnetic coil, away from the target area, and the length of time the device is to be held at that position may be determined.

These initial parameters may be selected as a first set of gross operational bounds, so as to calibrate appropriate coil to target distance, and/or to determine the appropriate treatment time periods. Accordingly, when running a calibration and/or positioning procedure, a treatment time, duration, and/or set point can be selected, e.g., via a drop down menu or via entering required text in accordance with a text box prompt, and the like. Particularly, the calibration treatment time may be selected so as to specify the time the coil will be maintained at each location as it moves sequentially from one grid location to another, such as prior to moving to the next grid location in the sequence. This procedure may be repeated a number of times, through one or more passes, e.g., 2, 3, 4, or more, in a manner so as to determine the appropriate positions that compose the treatment site, as well, as the device treatment delivery parameters.

Additionally, as set forth in FIG. 6D, a system operator, or a suitably configured A/I module of the system, may determine or otherwise implement a tracking procedure, which tracking procedure sets the bounds within which the targeting and/or treatment procedures may be implemented. For instance, the operator of the system may set a first set of parameters, such as for determining a target area within which a treatment operation may be performed, such as within which the imaging component may track the movements of the positioning element and/or tMS device. For example, a tracking pattern may be configured such as by the operator entering, and/or the system automatically determining, the parameters for performing a targeting procedure, from which procedures a set of parameters for running a treatment procedure may be determined.

Figure 7A:
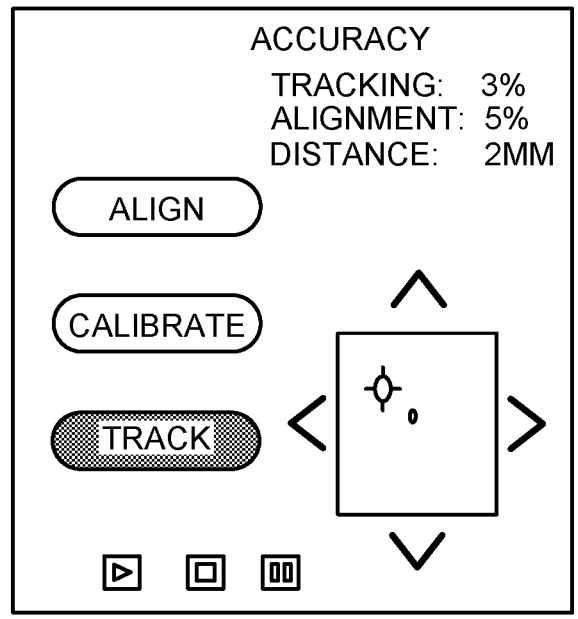
FIG. 7A provides a representation of a GUI for displaying data pertaining to a misaligned tracking operation of the system.
Figure 7B:
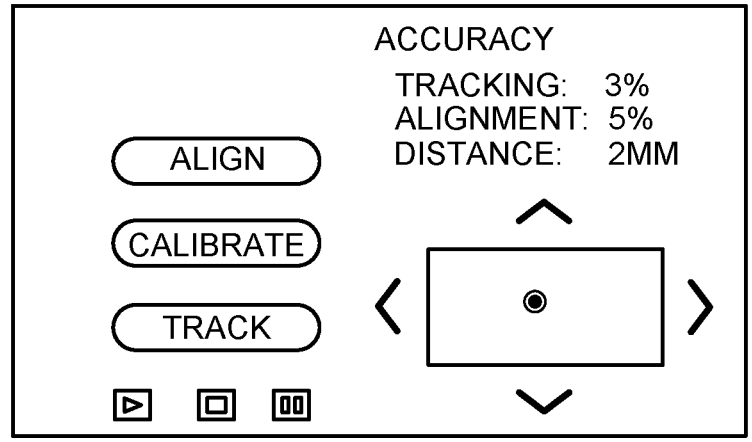
FIG. 7B provides a representation of a GUI for displaying data pertaining to an aligned tracking operation of the system.

Particularly, when configured for manual selection, the user interface may present a number of parameter dimensions that are to be selected or otherwise chosen by the operator, such as by entering the determined value into a text prompt. These parameters may include a minimum and maximum value (or range) for one or more of: a tracking region, a treatment region, a tracking movement time, a treatment movement time, number movements, a tracking and/or treatment distance, positioning coordinates, target and/or treatment area coordinates, and the like. For example, FIGS. 7A-7B, present a GUI for performing a tracking procedure. Particularly, although this may be performed automatically by the system, in various embodiments, this may be performed, or at least initiated, manually, such as by deselecting a tracking protocol at the GUI.

More particularly, as shown in FIG. 7A, a tracking accuracy progress screen is depicted, in this instance evidencing a misalignment. The misalignment can be illustrated in any suitable form, but in this instance, it is demarcated by a target alignment illustrated by a dark dot, and the actually alignment, which is illustrated by an open circle. As can be seen with respect to FIG. 7A, the open circle of the actual alignment is offset from the dark dot representing the target alignment. However, as set forth in FIG. 7B, the open circle overlaps the targeted dark dot, thereby indicating that the actual alignment coincides with the targeted alignment. Hence, when a misalignment occurs, as exemplified in FIG. 7A, a new alignment protocol may be implemented so as to ensure the proper targeting alignment has been procured, either manually or automatically by the system. Accordingly, the GUI can display tracking and alignment accuracies, which may be displayed graphically and or descriptively by one or more texts boxes, such as a text box indicating a degree of tracking, alignment, and/or distance with respect to an optimal targeted alignment.

Additionally, as can be seen with respect to FIG. 6D, along with the tracking settings, the distance sensor settings may also be determined, for instance, a sensor "on"/"off" button may be deselected, which when selected will allow for selecting the parameters for configuring the distance sensor parameters. For example, where the system sensors incorporate a time of flight module and/or torque-force sensor, the operational parameters for these sensors may be entered into the system, such as the TOF offset, and/or the force threshold and force retreat distance may be entered. Specifically, the torque force sensor may be configured for retracting and withdrawing the positioning element and/or tMS device if a treatment subject makes contact with one of the device components, such as accidentally, such as where such contact can cause harm or pain to the subject. However, by setting a minimal contact force, when such a force is encountered, the devices of the system may be automatically withdrawn automatically.

Additionally, with respect to the imaging component and/or a distance sensor, a determined distance configuration can be entered into the system, e.g., at the GUI, such as for automatically positioning the positioning element and/or tMS device into a predetermined configuration, and/or the GUI can give real-time feed back of the present position of the positioning element and/or the tMS device, such as via real-time, time-of-flight sensing. The network setting and communications protocols can also be adjusted via the presented GUI. Accordingly, the system may be configured for real-time targeting and tracking of the targeting and treatment space as well as the movements of the positioning element and tMS devices within that space.

For instance, once one or more treatment areas have been defined the system itself, or an operator, can initiate a therapy session where one or more magnetic pulses may be applied to the treatment area/site such as for the alleviation of pain thereby. In particular instances, the application of the therapy may be conducted with target area tracking, and may continue until complete, paused, or stopped by the operator, or if there is an unexpected contact between the subject being treated and a device of the system. During treatment the system may be configured to monitor positioning of the positioning element and/or tMS device with respect to the target and/or treatment area marker element(s) positions, particularly, as with respect to a primary and/or a secondary marker placed proximate the target and/or treatment areas. Such positioning may be monitored and/or tracked via the imaging component, e.g., camera, and/or the distance sensor, e.g., the time-of-flight sensor, which monitoring and/or tracking may allow the system controller to receive and process this data to monitor and track any patient position changes, and in view of which to calculate new target position values. Likewise, in light of the new positioning calculations, the controller can then direct the movements of the positioning element and/or tMS device to the new target positions thereby tracking the target and/or treatment areas.

Accordingly, the system can be configured so as to provide feedback to and between the various components of the system, such as between the positioning element, tMS device, the imaging component, the distance measuring sensor, the control unit, and the like. If at any given instance the position feedback is lost the positioning element may then stop treatment and/or maintain the current position and/or return to the last tracked location. This may occur in an instance where the primary tracking marker element loses connectivity with the distance scanner. In such an instance, the last known position values of the primary and/or secondary marking devices may then be used to re-initiate and/or continue target and treatment area tracking. For instance, the secondary marker can be employed to continue the tracking, and once connectivity with the primary marker becomes available again the positioning element may once again be stopped at its current location, and/or restarted once full connectivity has been reestablished. Then the position marking elements of the primary marking device may be used again for position tracking.

Particularly, in view of the above, FIG. 8 presents a methodology for performing a targeting and/or treatment procedure. For instance, FIG. 8A presents a start screen at a graphical user interface for the implementation of one or more procedures of the system, including an interface for moving the system components to a home or targeted, e.g., a previously determined target, position, a calibration interface, such as for calibrating an imaging element, e.g., a camera, with the positioning element, e.g., a robotic arm, and/or a target and/or treatment region. A start or a complete interface may also be provided. Specifically, by engaging the home or targeted interface, the various components of the system may be retracted from any position they are in so as to return to a home position, of they may be moved from a starting position, e.g., a home position, and be moved into a pre-defined targeted position, respectively.

Figure 8A:
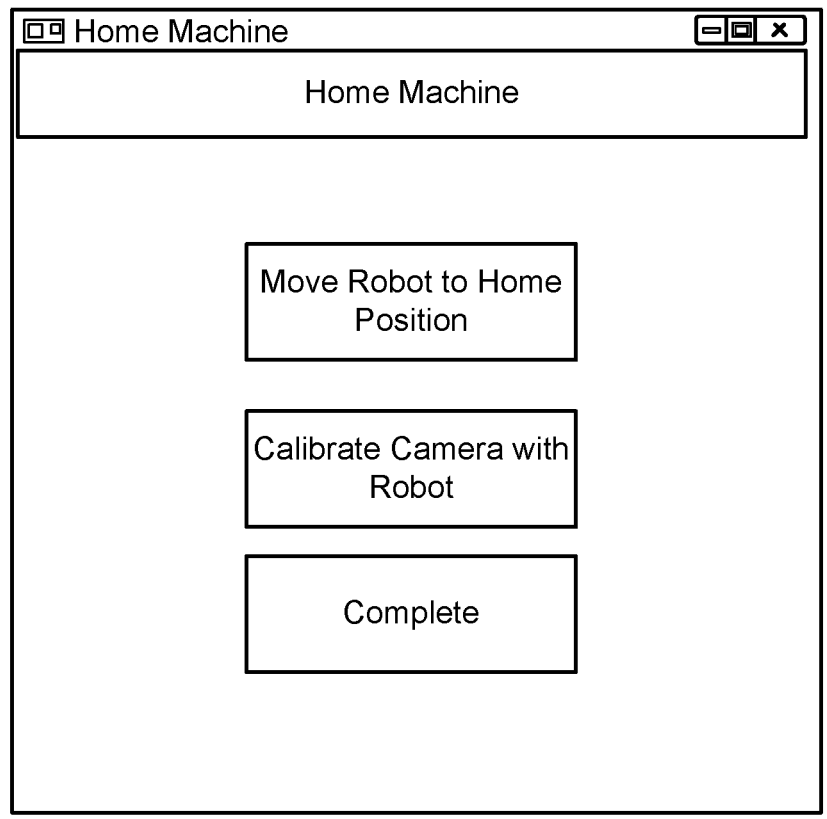
FIG. 8A provides a representation of a GUI displaying data a menu for selecting a process to be run by the system.
Figure 8B:
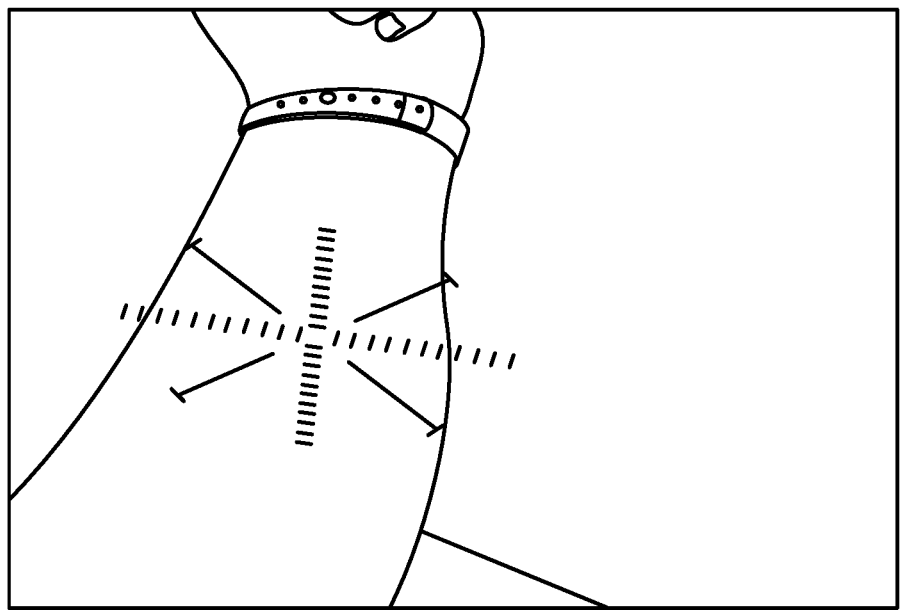
FIG. 8B provides a representation of a 3D matrix that may be used for determining the appropriate targeting for treatment.

Likewise, as set forth in FIG. 8B, if a calibration interface is engaged, a targeting procedure may be implemented, as described above, wherein a virtual representation of a target area may be generated and applied, such as in a virtual manner, to the target area. Specifically, as can be seen with respect to FIGS. 8B-8C, the system may be configured for generating and/or displaying a target area, such as near the region to be treated, or as a virtual representation of the target area presented at the graphical user interface of the display, as exemplified by FIG. 8D. For instance, as exemplified in FIG. 8B, a target area may be projected onto a body part of the patient, e.g., the arm, such as where, in this instance, the projection is configured as a three-dimensional axis, such as including an X-axis, a Y-axis, and a Z-axis, which axes can be used to define the target area, and from there the treatment area may be determined.

Particularly, in various instances, once a target area is defined generally, a treatment area may then be defined. For example, in a particular embodiment, a grid-matrix may be generated and, in some embodiments, may be projected onto the body part to be treated, so as to provide a framework within which a targeted area may be tested so as to determine its amenability, e.g., reactivity, for treatment. More specifically, as discussed above each box in the grid represents an area to be tested, such as in an iterative process by moving the tMS device in a manner to deliver one or more magnetic impulses to each of the demarcated areas, e.g., 1-9, so as to determine the reactivity of each area to the magnetic treatments, whereby each area that is determined to be reactivity represents and/or otherwise defines one or more treatment sites. As can be seen with respect to FIGS. 8C and 8D, the target site represented by area 5 is reactive to the treatment, and thus, can be subjected to further testing to define one or more particular treatment sites.

Figure 8C:
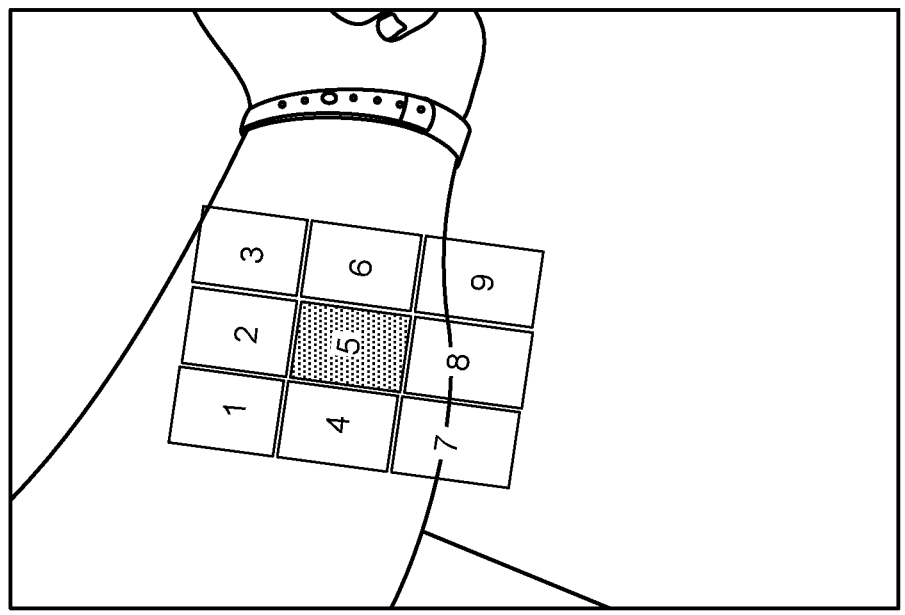
FIG. 8C provides a virtual matrix that can be used in determining one or more sites for treatment.
Figure 8D:
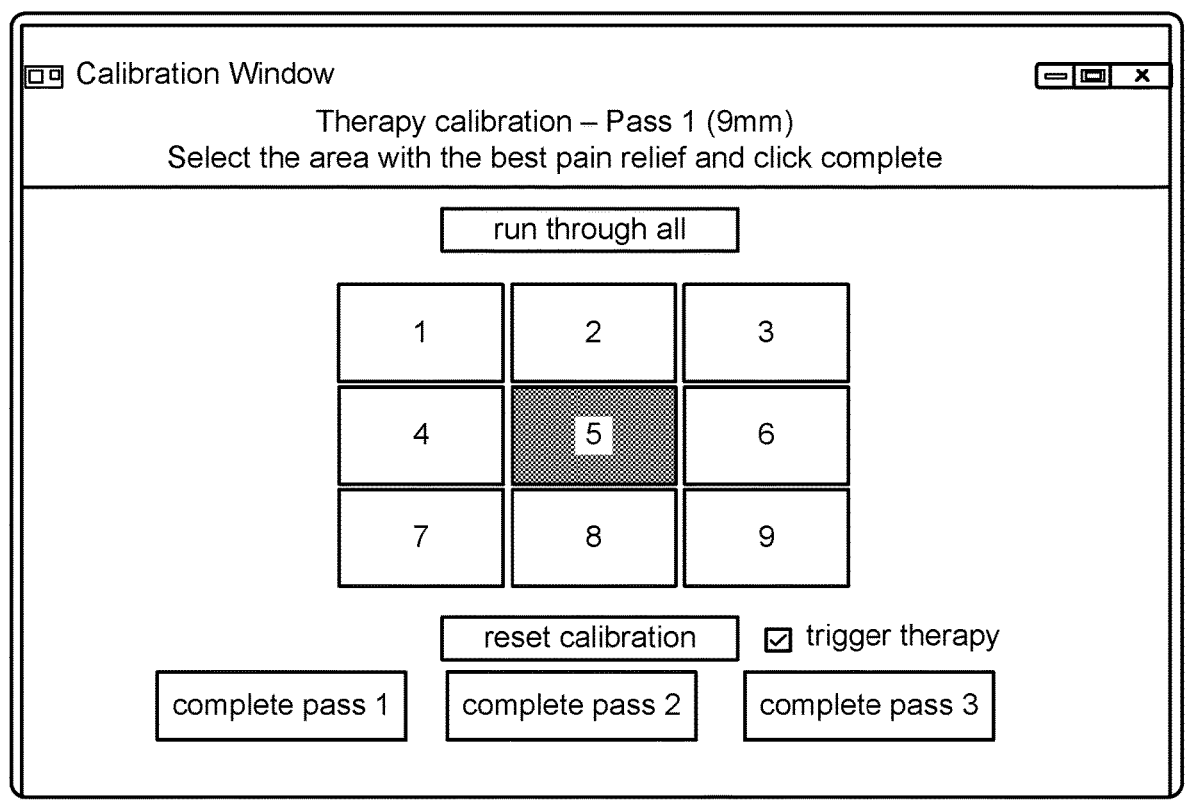
FIG. 8D provides a graphical representation of the virtual matrix of FIG. 8C as presented at a GUI for use in targeting and applying treatment.
Figure 8E:
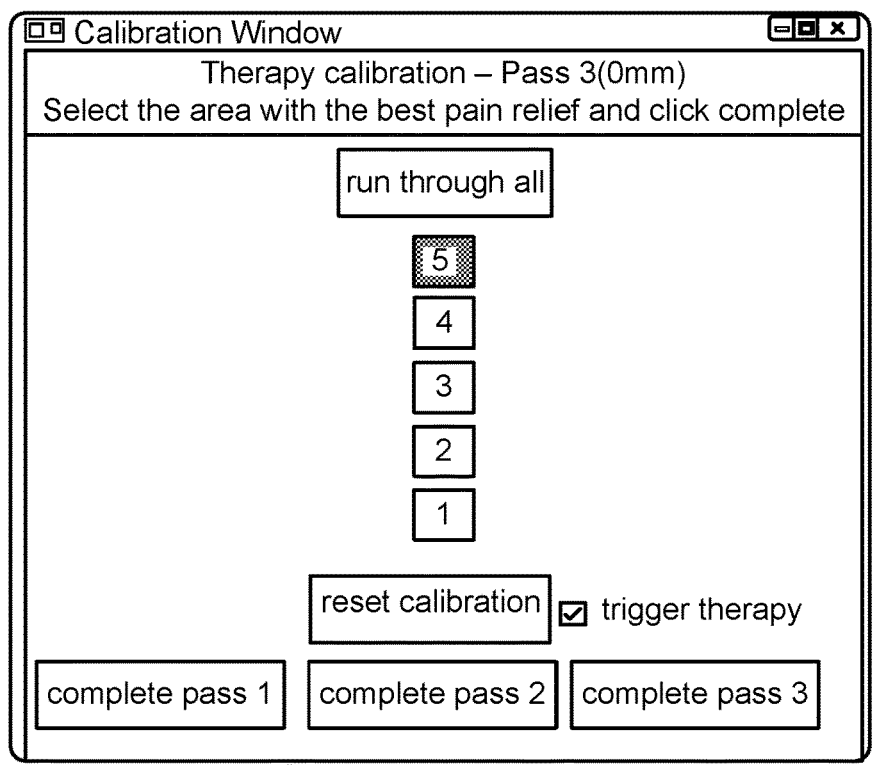
FIG. 8E provides a graphical representation for determining a depth of focus for the application of a magnetic field.
Figure 8F:
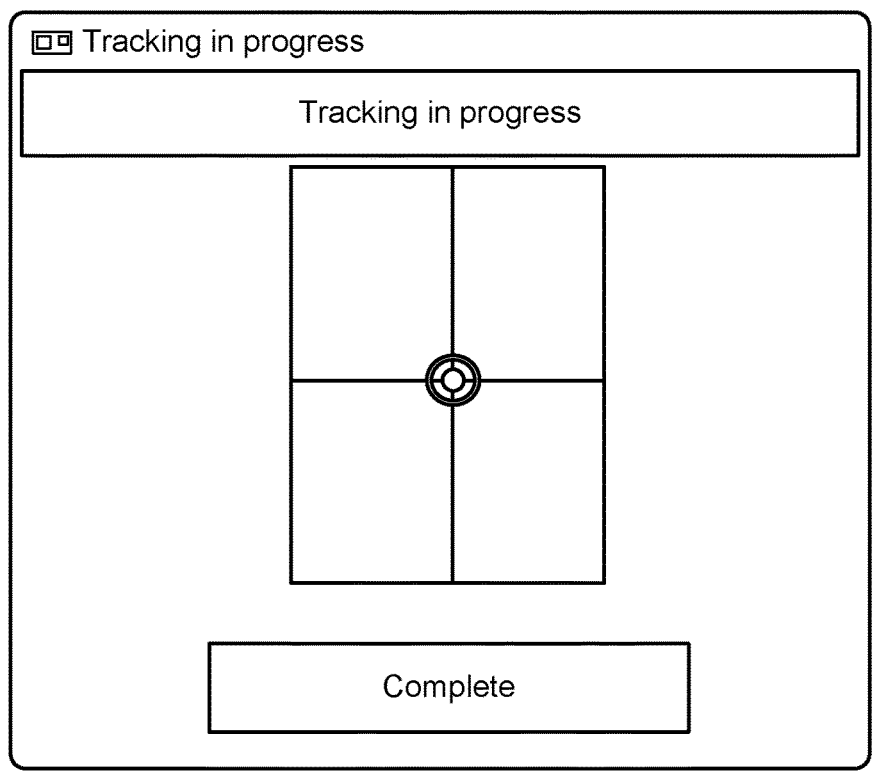
FIG. 8F provides a graphical representation indicating that the alignment protocol has been successful indicating that the device is appropriately aligned.

In particular instances, the projected grid matrix, as illustrated in FIG. 8C, may be modeled virtually at the graphical user interface, as illustrated in FIG. 8D. However, in other instances, the projected grid matrix need not be used, rather, only the virtual matrix need be presented for performing the targeting procedures. More particularly, as represented in FIG. 8E, once a treatment area has been determined, in this instance area 5, e.g., so as to define the X and Y planes of the treatment area, such as in a first and second pass, a further pass may then be implemented so as to determine the Y-axis dimension of the treatment site, such as to determine the depth for the treatment application. Accordingly, once a treatment site has been determined and its dimensionality defined, such as with respect to its X, Y, and Z coordinates, then the positioning element and tMS device may be aligned to the treatment site, and the alignment procedure may be completed, such as exemplified in FIG. 8F, where the treatment alignment is shown to correspond to the target alignment.

It is to be noted that in various instances, a system fault or interruption may occur, such as if an unintended contact occurs between the tMS device and/or positioning element and the treatment site. Upon such an occurrence, e.g., of a system fault, the tMS device will stop applying a magnetic field, and/or the positioning element will retract, and the current sequence/operation will be aborted. In such an instance, the fault condition may be removed and the fault message may be acknowledged by the operator. Each sequence may then be restarted. An emergency stop may also be implemented manually by the operator or the subject receiving treatment.

In various instances, the system may include an artificial intelligence (A/I) module that may include a learning or training platform that is configured for collecting and/or otherwise receiving data, e.g., pertaining to a collection of treatments of a single or multiple subjects, aggregating and/or compiling data, and then processing the data for the purposes of one or more of: learning the voice and words or phrases of a user, such as an operator and/or subject to be treated, learning the optimal treatment conditions, including positioning and orientation for efficient and effective delivery, and/or learning optimal administration parameters, such as regards the strength, frequency, amplitude, depth, duration, and/or other wave quality characteristics for modulating the magnetic pulse to be delivered to the subject for treatment. For instance, as described above, in various instances, the system may be configured for being operated manually, such as by a trained operator, whereby the system assist the operator in the performance of their operation of the system. However, in other instances, the system may be adapted for being configured and/or operated autonomously and/or automatically, such as by the subject to be treated, e.g., for individual home use. In either instance, the system may be configured for receiving a voice command, e.g., one or more instructions with regard to the administration of a treatment, and then performing that treatment in response the received instructions.

Additionally, the system may further include an inference engine that is configured for: predicting one or more of the meaning behind the words and/or phrases employed by users, especially with respect to their use of the system to orientate the device and perform a treatment; to develop one or more set of rules or instructions based on an analysis of the collected data with respect to pain experiences and system configurations for the effective and efficient administrations of treatment; and/or for analyzing user feedback so as to learn individualized treatment parameters in order to make treatment personalized to the subject to be treated.

As such, the system is capable of receiving voice or other entered commands and/or use parameters from a plurality of users and patients with regard to their receipt of treatments. In particular instances, as indicated above, the system may include a downloadable app that is capable of being downloaded and/or otherwise installed on a user device, e.g., a desktop, laptop, or other mobile computing device that may be a smart phone or computing watch. For example, a computing device configured as a mobile phone, or a wrist-worn watch may be provided, where the mobile device includes a display screen upon which a graphical user interface of the system may be presented. The voice command may be in natural language, while computer derived commands may be in a computer language implemented in the system.

Upon receiving a voice or other command, such as an instruction pertaining to the configuration of the system and/or to receiving a treatment thereby, the system, via an associated controller and/or the mobile computing device, may then transmit the voice command to the central server of the system, particularly to the A/I module of the system. The A/I module may be configured to include a voice recognition and/or modulation module that is capable of receiving and determining the meaning behind a user's voice and/or other entered commands, and may then initiate one or more routines within the system to effectuate the users command, such as with respect to effectuating the configuration of the system and/or the administration of treatments. The voice data and/or other user entered commands may be received and/or entered into the system via a suitably configured application programming interface, API. Once received by the system, the command may be interpreted by the system, e.g., a speech recognition application, whereby the language will be parsed, and relevant data, e.g., configuration data and/or treatment delivery data, may be entered into the system. The system may then forward a confirmatory message back to the device of the user so as to allow the user to confirm that the system has correctly interpreted the voice or other commands.

For example, the system may automatically determine the relationships between different users and their preferences and habits, e.g., with respect to their receipt of treatments, and in turn the system can determine the same for other users experiencing the same or similar pain at the same or similar locus, such as due to the same or similar nerve damage. Accordingly, the system may include a searchable database that anonymizes patient data, but then allows the treatment parameters and user feedback data to be searched by the system and be employed thereby to determine one or more trends and/or usage factors that may be implemented in developing personalized or universal rules for delivering of treatment to one or more subjects. Accordingly, the Artificial Intelligence Module may be used to gather and/or harvest collected data about users and their experience of pain and their treatment parameters, which information may be employed by the system to make predictions, suggestions, and/or weight, and/or adjust potential usages of the system by the user with respect to the pain they experience and treatments they receive in response thereto. This data may be collected by the system and may be fed into the A/I module, e.g., a machine learning platform, and may then be used as data points to form and/or structure a searchable database of the system.

In this manner, all of the treatments, e.g., pain experience, pain location, and treatment configurations, implemented by users of the system, and their usage patterns may be collected and analyzed by the system so as to determine useful patterns of treatments and pain alleviation to better assist the treatment needs and/or patterns of its users, in general, or specific to any given particular user. Once collected, the data may then be structured into a table or graph, or other relational infrastructure, such as a hash table or data tree or knowledge graph that may then be used to identify correlations and/or relationships between the data, such as between pain experience and/or location and treatment parameters and/or system configurations.

Such relationships may then be weighted and mined to determine correlations between those experiencing, or not experiencing pain amelioration, the treatment parameters and configurations that have led, or not led, to that amelioration, the treatment sites and configurations, as well as various other subject related factors that may be relevant to the effectiveness of treatments, such as other medical or physiological conditions the subject may have, such as exemplified by their genetic code and/or their electronic medical or personal health records, and the like. This data may then be fed into an artificial intelligence engine of the system to determine and/or predict patterns in treatment parameters, configurations, and effectiveness of treatments. Additional information may also be collected and used to understand, evaluate, and characterize subject and/or usage patterns, make predictions and/or suggestions about treatments and configurations, as well as timing and length or duration of treatments. These analyses allows for a great quantity of data to be collected and analyzed so as to derive one or more conclusions, such as a conclusion as related to treatment parameters.

For instance, the A/I component may include an analytics engine that may be configured for performing both a learning function, such as through review of historic data, and to generate rules by which to determine positioning, configuration, and treatment parameters and/or predict future treatment effectiveness patterns. As indicated above, once collected, the data may be searched, and may be run through a suitably configured analytics module, such as an artificial intelligence engine, to identify treatment parameters, device configurations and orientations, and pain experience factors from various different sources that may be in some way correlated with one another, and therefore, may be used to predict effective treatment parameters, such as on a personal or global basis.

Particularly, the data from all various sources may be collected and organized in a structure that is specifically designed to pinpoint correlations between otherwise unknown relationships. Such a relational architecture may take many forms, such as in the form of a Structured Query Language (SQL), Hierarchical Tree, or Knowledge Graph database. Collected information, for example, may be run through one or more computational and/or analytics regimes, as herein described, so as to identify pertinent known or inferred data points from which various relationships between producers, consumers, and delivery agents engaged with the system may be determined, and motifs in their usage may be explored, and future patterns predicted.

Accordingly, in one aspect, presented herein is a system including an interactive, communication platform that is adaptable so as to provide for real-time pain characterization and/or treatment regimes that is constantly kept up to date, moment by moment, by a server network of the system. In particular embodiments, the platform may include one or more, e.g., a plurality of, client application programs, e.g., controlling one or more treatment apparatuses, such as a disperse network of device computing controllers, which controllers may be in communication with a nationwide server or bank of servers, through which the client applications the various devices of the system may communicate with one another and/or the system. The system may also include one or more of an analytics module, for performing data analysis; and an artificial intelligence module, for generating a searchable data structure, e.g., a knowledge graph, through which data may be correlated, relationships determined or inferred, and future behaviors, e.g., subject response to treatments, may be predicted.

Hence, an important aspect of the system is an Artificial Intelligence (A/I) module having one or more of a learning or training platform, including a learning engine, and an analytics or inference platform, including an inference engine. In one instance, the learning platform includes a processing engine that is configured for taking known data, e.g. device use parameters and/or treatment results data, running a learning and/or training protocol on the data, and developing one or more organizing rules therefrom. Likewise, the analytics processing platform includes a processing, e.g., inference, engine that is configured for applying the rules developed by or for the learning platform and applying them to newly or previously acquired data to generate one or more outcomes thereby, such as where the outcome may be a known or inferred relationship, a known or predicted result, and/or a probability of one or more outcomes, and the like. In various instances, the inference engine is configured for continuously running analytics on received data on a daily basis and/or with regard to one or more treatment regimes.

As indicated above, in one particular embodiment, the A/I module is configured for determining correlations between the various data collected by the system. For instance, in various instances, the A/I module may be configured for generating a data structure, e.g., a knowledge graph, wherein the various data collected by the system, e.g., treatment configurations, device orientations, pain locations, etc., are uploaded into the graph as a constellation of data points. In such an instance, the learning engine may be configured for taking known rules to determine known relationships between the known data points, and from these known data, the learning engine may be configured for inferring unknown relationships between data points to determine heretofore unknown relationships between the data points, which in turn may be used to determine new rules by which to determine other unknown data points, relationships between the two, and/or to make one or more predictive outcomes, e.g., effectiveness of a treatment regime, based on the known and/or learned data, such as in response to one or more queries. For example, the data, the relationships between the data, and the determined and/or inferred rules may be employed to generate a data structure, such as a knowledge graph, and/or to mine the various data within the system to generate an answer to a query and/or a suggestion, e.g., of the effectiveness of a treatment parameter. Accordingly, a unique feature of the A/I module is its predictive functionality, which functionality may be implemented by a predictive analytics platform that is configured for performing one or more predictive analyses on the obtained and/or generated data, such as by generating one or more predictive outcomes.

Further, once determined, the system, e.g., via the suitably configured learning platform, may be adapted to configure or suggest device configurations for treatments of subjects experiencing the same or similar pain, such as by the artificial intelligence module increasing or decreasing a weighting scale used to weight the connections between various influencing factors and user actions and/or outcomes of those actions, such as where various treatment parameters are identified with treatment effectiveness based on subjects experiencing the same or similar amelioration of pain with the same or similar system configuration. For instance, in such instances, when various patterns are formed, the system may learn these patterns, determine the presence of one or more trends, or other factors of import, and/or predict a likely manner in which the user will behave in response to treatments, and the level of confidence may be given to the predicted outcome, such as from 0.0, not very likely to 1.0 almost completely certain. Accordingly, when the system makes a correct prediction, the connection between the initiating action and the presence of a trend in that action, as well as the connection between the action and a predicted outcome of that action, may be strengthened, such as by giving an estimation of the presence of a trend and/or a predicted outcome in the future, for the same or substantially similar circumstances, more weight. In a manner such as this, the system may be configured to keep track of the various patients being treated by the system so that the various identified factors that may be influencing the emergence and/or maintenance of such patterns may be identified, predicted, and employed for determining treatment parameters and configurations for the treatment of other patients seeking pain relief.

Specifically, the system may generate and employ one or more data structures that may be queried so as to predict the answer to one or more questions. For instance, as described in detail herein, the system may be configured for receiving and analyzing information with regard to a plurality of patients being treated, which information may include a characterization of the experience of pain, site of pain, morphology of treatment site, effectiveness of treatments, and/or configurations and orientations of the system pertaining thereto, which data once collected may be incorporated into a data structure of the A/I module. For these purposes, the system may present one or more subjects and/or operators a series of questions, such as via an automated interview process, the responses to which may be used to characterize the subject's response to treatment. Additionally, the system may automatically track how the subject responds to the treatments administered by the system, as well as the attendant data pertaining thereto, such as data related to device configuration and/or orientation, and treatment parameters, such as time, duration, strength, amplitude, frequency, and other parameters characterizing the magnetic pulse being delivered during treatment. All of this information may form data points that characterize any given subject of treatment and/or their experience of pain, and response to treatment.

These data points may then be employed as branches or nodes within a data structure, which data structure may take any suitable form, such as a data tree and/or a knowledge graph. From these various data points relationships between subjects being treated may be identified, and the connections between them may be weighted based on the number and form of the interactions between them. Hence, the more subjects respond to the treatments and/or system configurations with respect thereto, the greater the weighting will be between the various nodes that may be employed to define their interaction. Likewise, the more negatively subjects respond to treatments and/or system configurations with respect their to, the less (or more negative) weight will be given to define their interactions.

Accordingly, in a manner such as this, data points between the various branches or nodes in the data structure of the system may be used to generate correlations between the nodes and to weight those correlations so as to build a data structure thereby, such as a knowledge tree or graph, which may then be queried to determine other relationships not previously known and/or to predict the influence of external factors affecting the usage of the system, and/or to predict and weight potential outcomes based on a collective of usage patterns of how users are engaging with the system. For instance, a data structure, such as a relational or hierarchical or knowledge graph structure, may be generated by the system receiving known data about the various users of the system, e.g., producers or sellers, purchasers of goods, promotional event organizers, or other users of the system, and, via a suitably configured data management system, building a structure, e.g., a tree or constellation, of data points and drawing connections between the data points.

For example, the data to be entered into the database, may be used to structure and populate an inference engine, e.g., based on the graph, which engine may be employed for searching and/or otherwise performing queries, and may further be utilized by an artificial intelligence analytics engine for predicting outcomes and/or making suggestions as to system and/or device configurations. Consequently, subject and/or treatment configuration and/or effectiveness data may be obtained and entered into the system in a variety of different manners, and may include the storing of information in hierarchical or relational models, as well as in a resource description framework (RDF) file or graph, and the like. Such a procedure may be performed for a number of different users.

Accordingly, once generated, the data structure, e.g., knowledge graph, may then be queried along a number of lines so as to make one or more determinations with respect to the various relationships between the various branches or nodes of the graph. For instance, the system may be configured to automatically be queried to determine if there is a pattern by which one or more subjects are responding to the treatments in the same or similar, such as with respect to system and/or devices thereof being configured in the same or similar manner. Hence, in various embodiments, the system may be configured so as to be queried along a number of different parameters to determine and weight a number of different answers, and thereby make a variety of different predictions. These predictions may then be given a weighted score, such as to the probability of being correct, and based on that score, the system can self-correct so as to properly account and/or correct for the predicted response to treatments for those being or to be treated.

In a typical architecture for performing such functions, such as for performing a structured search query, for instance, the system may include a database. The database may include information pertaining to the detailed pain experience, site of pain, target and/or treatment site, system configurations, device orientations, treatment regimes, and the like. The database may also include characteristic data pertaining to the patients themselves, and/or relational data pertaining to their response to treatments. In such an instance, the relevant data points may be identified and pulled from the general database, and a localized or global data structure may be built.

Any data structure may be employed for performing the search in question, in various instances, however, the data structure may be a relational data structure, such as a Structured Query Language (SQL) database, which may be implemented via a relational database management system, or the data structure may be a hierarchical, or graph based data structure. For instance, in one implementation, a SQL database is presented, which database may be a table based data structure, such as where one or more tables form the base structure wherein data may be organized and stored, such as in a variety of columns and rows, searched, relations determined, and queries answered in a structured manner. Particularly, in such an instance, SQL statements may be used to structure, update, and search the database.

In various embodiments, a table-based database may be presented, e.g., a relational database structure, which data structure may be searched, and used to determine relationships from which answers to one or more queries may be determined. Typically, in such a data structure, identifiers, such as keys, are used to relate data in one table to that in another table. Accordingly, provided herein is a database that may be built and structured as a structured query language (SQL) database that has a relational architecture, and may be managed by a data management system, such as a relational database management system (RDBMS). In particular instances, a series of tables, for instance, may be employed by which correlations may be made in an iterative fashion.

Accordingly, a key, such as an electronic medical record identifier, may be used to correlate the tables, which key may be accessed in response to a question, prompt, or command, such as how the patient is responding to treatment administered by the system when the system is in a particular configuration, and/or how that response changes when the system configuration changes. In various instances, the key may be any common identifier or an encrypted identifier employed to keep the subject's identity private. Accordingly, without the key it becomes more difficult to build correlations between the information in one table with that of another. In certain instances, the table may be a hash table and a hash function may be employed in search the table for correlations with other data structures.

A further architecture that may be used to structure a database is a hierarchical data structure. For instance, in various instances, the database may be structured as a data tree, e.g., a suffix or prefix tree, where various data elements may be stored in a compressed, but in correlated fashion, where the various roots and branches form divergent data points with respect to potential correlations. Specifically, in such an instance, the data may be stored within the data structure in such a manner that the stored records are connected with one another through relational links, such as where the various records are a collection of fields that store data files in a chain of superior and subordinate levels of organization, such as in a pyramidal or other hierarchical configuration.

In other instances, a graph-based architecture may be structured and used to determine the results for one or more queries. Particularly, a knowledge graph architecture may be employed to structure the database; so as to enhance the performance of computational analyses executed using that database. Such analyses may be employed so as to determine whether a given user's present use of the system comports with their past use and/or comports with how other users in general, e.g. the average user, have or are presently interacting with the system, such as with respect to the present user's scoring of a given event and/or performer in the event, and/or with respect to their regular pattern of usage.

In a manner such as this all of the treatment protocols, system configurations, device orientations, patient responses to treatment, as well as patient and operator feedback for one or more subjects, such as for all subjects being treated, may be organized and stored by the system in a dedicated database, such as a health management database, wherein the data to be stored may be tagged, characterized, grouped into one or more categories, e.g., based on pain experience, and may then be stored in a structured architecture as described above. Specifically, in various instances, the treatments and patient feedback being tracked within the system, as well as all the various data associated with the treatments may be tracked by any suitable tracking system, but in some instances, may be tracked by a suitably configured blockchain mechanism.

An additional feature of the system is that it provides a more personalized health management experience for the subject being treated. For instance, the system may track patient pain experience and response to treatments, and may as well track their other health and/or dietary characteristics, and/or may track other patient experiences having a similar or same experience. Such tracking may be performed throughout the system, trends with regard to treatment effectiveness may be identified, and the system may then make suggestions to the operators and/or patients receiving treatment based on previously administered treatment regimes that have been shown to be effective in the treatment of others having the same or similar characteristics of their pain experience. For example, the system may track and analyze all relevant information regarding the patients experiences of pain and the system configurations that have led to a decrease in pain experience for those subjects, and can make treatment suggestions based on the system's analysis of the collective of patients being treated, their pain experiences, their pain locations, and their responses to treatments, as well as the configurations of the system and devices thereof with respect to those treatments administered.

In particular instances, to facilitate one or more of these implementations, a software and/or hardware application may be present and executed by one or more of the system controlling and/or treatment devices and may provide a user interface that can display information from or about a subject to be treated and/or device configurations and/or status monitoring device(s) and/or the control device. The interface may further provide input portions that permit the user to enter information and/or commands. For instance, such a software application may be in the form of a "mobile app" for use on or execution by a mobile smartphone or dedicated device or processor thereof, or may be in the form of a software application for execution in a conventional personal computer (e.g., desktop or laptop or tablet) or enterprise computer system.

For instance, an exemplary software application may present a user with a one or more menus or screens configured at least for permitting viewing and/or selection of user preferences or settings, for viewing data received from or related to one or more treatment modalities and/or system component configurations and for controlling said functions and/or determining the positioning of the various components of the system. In addition to such control and presentation of wireless (or wired) communications, communication features may include transmission of commands and settings, receipt of sensor data, feedback data, and/or historical use data, alarm/warning notifications (e.g., at loss or attainment of proximity), etc., all of which may be collected by the system, be stored within a database, and be retrieved and analyzed by the system to suggest future use protocols.

Hence, in various instances, implementations of various aspects of the disclosure may include, but are not limited to: apparatuses, systems, and methods including one or more features as described in detail herein, as well as articles that comprise a tangibly embodied machine-readable medium operable to cause one or more machines (e.g., computers, etc.) to result in operations described herein. Similarly, computer systems are also described that may include one or more processors and/or one or more memories coupled to the one or more processors. Accordingly, computer implemented methods consistent with one or more implementations of the current subject matter can be implemented by one or more data processors residing in a single computing system or multiple computing systems containing multiple computers, such as in a computing or supercomputing bank.

Such multiple computing systems can be connected and can exchange data and/or commands or other instructions or the like via one or more connections, including but not limited to a connection over a network (e.g. the Internet, a wireless wide area network, a local area network, a wide area network, a wired network, a physical electrical interconnect, or the like), via a direct connection between one or more of the multiple computing systems, etc. A memory, which can include a computer-readable storage medium, may include, encode, store, or the like one or more programs that cause one or more processors to perform one or more of the operations associated with one or more of the algorithms described herein.

Any of the features or attributes of the above the above described embodiments and variations can be used in combination with any of the other features and attributes of the above described embodiments and variations as desired. From the foregoing disclosure and detailed description of certain disclosed embodiments, it is also apparent that various modifications, additions and other alternative embodiments are possible without departing from the true scope and spirit.

The embodiments discussed were chosen and described to provide the best illustration of the principles of the present invention and its practical application to thereby enable one of ordinary skill in the art to utilize the invention in various embodiments and with various modifications as are suited to the particular use contemplated.

All such modifications and variations are within the scope of the present invention as determined by the appended claims when interpreted in accordance with the benefit to which they are fairly, legally, and equitably entitled.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present disclosed embodiments have been specifically disclosed by representative configurations and optional features, modification and variation of the embodiments herein disclosed may be resorted to by those skilled in the art, and that such modifications and variations are considered to be within the scope of this disclosure.

Specific embodiments have been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

The invention claimed is:

1. A system for delivering transcutaneous magnetic stimulation (tMS) to a treatment site on a peripheral body portion of a subject, the system comprising:
a tMS application system, the tMS application system comprising:
a tMS device configured for delivering a focused magnetic flux to the treatment site when positioned proximate the peripheral body portion of the subject, the tMS device comprising:
a housing having an extended body, the extended body including a proximate portion having a proximate end, and a distal portion having a distal end, the extended body defining a cavity for retaining one or more components of the tMS device, and,
an insulated magnetic coil unit including a magnetic coil disposed within the proximate portion of the extended body of the housing, the magnetic coil unit configured for generating and delivering a focused magnetic flux at a determined pulse rate, and
a magnetic flux controller in communication with the magnetic coil unit and a pressure sensor, the magnetic flux controller configured to control the focused magnetic flux and the pulse rate to be delivered by the magnetic coil of the tMS device so as to deliver tMS to the treatment site of the subject;
a positioning element having a proximal portion including a proximal end, and a distal portion including a distal end, the distal portion being coupled to the magnetic coil unit proximate the distal end, the positioning element being composed of a plurality of articulating arm members, the articulating arm members being configured for both planar and rotational movement, at least two of the plurality of articulating arm members being coupled together by an automating element comprising one or more motors configured for providing automatic movement along one or more of an X, Y, and Z plane as well as rotational movement about each X, Y, and Z axis, the automating element for positioning and orienting the tMS device proximate the treatment site, the positioning element including a positioning element controller configured for controlling the automating element so as to effectuate the positioning and the orienting of the tMS device;
an imaging component, the imaging component including one or more image capturing devices, each image capturing device being configured for capturing one or more images defining a three-dimensional space, the three-dimensional space being occupied by one or more of at least a portion of the peripheral body portion of the subject, the tMS device, and the positioning element, the imaging component being configured for communicating the one or more images defining the three-dimensional space over a network;
a distance scanner coupled to the housing of the tMS device, the distance scanner being configured for generating and communicating distance data, the distance data including a determination of a distance between the magnetic coil unit and the treatment site on the peripheral body portion of the subject to be treated;
the pressure sensor, coupled to the housing of the tMS device, the pressure sensor being configured for sensing a near contact with a portion of the peripheral body portion of the subject, generating proximity data, and signaling for the retracting of one or more of the positioning element or the magnetic coil unit if a proximity limit is threatened to be breached; and
a control module communicably coupled to the positioning element controller of the positioning element, the magnetic flux controller of the tMS device, the imaging component, the distance scanner, and the pressure sensor, the control module being configured for:
receiving the images of the three dimensional space, the distance data, and the proximity data,
employing the images of the three dimensional space and the distance data so as to track movements of the positioning element, the magnetic coil unit, and the treatment site, and to align the magnetic coil unit with respect to the treatment site,
generating control instructions for directing the automating element in moving one or more articulating arm members of the positioning element autonomously so as to orientate the magnetic coil unit relative to the treatment site on the peripheral body portion of the subject, and
employing the proximity data so as to maintain, at near real time, an optimal distance between the magnetic coil and the treatment site despite any movements of the peripheral body portion proximate the treatment site, the control module including a communications module for communicating the control instructions to one or more of the positioning element controller and the magnetic flux controller prior to the delivering of transcutaneous magnetic stimulation to the treatment site on the peripheral body portion of the subject.

2. The system in accordance with claim 1, wherein the magnetic coil of the tMS device further comprises a plurality of coils, the plurality of coils being arranged in such a manner as to generate a magnetic field between them, the generated magnetic field having an amplitude greater than an amplitude than that which either coil could generate individually by itself.

3. The system in accordance with claim 1, wherein the determined pulse rate of the magnetic flux generated by the tMS device has a frequency within the range from about 0.2 Hz to about 5 Hz.

4. The system in accordance with claim 3, wherein the positioning element comprises a robotic arm.

5. The system in accordance with claim 4, wherein the pressure sensor comprises a torque-force sensor.

6. The system in accordance with claim 5, wherein the system further comprises a cloud based server coupled to a database, the cloud-based server being configured for processing image data so as to produce results data, and the database is configured for storing one or more of the image data and the results data.

7. The system in accordance with claim 6, wherein the control module is configured for communicating with the cloud-based server over the network, and further configured for receiving and implementing one or more instructions, the one or more instructions pertaining to positioning the tMS device in an optimal placement for the delivery of tMS to the treatment site.

8. The system in accordance with claim 7, wherein the control module is coupled to a display device for displaying a graphical user interface of the system, the graphical user interface being configured for allowing substantially real-time tracking of movements within the three-dimensional space.

9. The system in accordance with claim 4, wherein the control module is further configured for controlling one or more of the tMS device, the positioning element, the imaging component, and the distance scanner in a manner to define coordinates of the treatment site within the three-dimensional space.

10. The system in accordance with claim 7, wherein the control instructions include directions for controlling one or more of a current, a voltage, an amplitude, and the pulse rate to be generated by the magnetic flux controller of the tMS device.

11. The system in accordance with claim 10, wherein the voltage to be generated is within a range from about 700V to about 1200V.

12. A system for delivering transcutaneous magnetic stimulation (tMS) to a treatment site on a peripheral body portion of a subject, the system comprising:
 a tMS application system, the tMS application system comprising:
  a tMS device configured for delivering a focused magnetic flux to the treatment site when positioned proximate the peripheral body portion of the subject, the tMS device comprising:
   a housing having an extended body, the extended body including a proximate portion having a proximate end, and a distal portion having a distal end, the extended body defining a cavity for retaining one or more components of the tMS device, and,
   an insulated magnetic coil unit including a magnetic coil disposed within the proximate portion of the extended body of the housing, the magnetic coil unit configured for generating and delivering a focused magnetic flux at a determined pulse rate, and
   a magnetic flux controller in communication with the magnetic coil unit, the magnetic flux controller configured to control the focused magnetic flux and the pulse rate to be delivered by the magnetic coil of the tMS device so as to deliver tMS to the treatment site of the subject;
 a positioning element having a proximal portion including a proximal end, and a distal portion including a distal end, the distal portion being coupled to the magnetic coil unit proximate the distal end, the positioning element being composed of a plurality of articulating arm members, the articulating arm members being configured for both planar and rotational movement, at least two of the plurality of articulating arm members being coupled together by an automating element, the automating element for positioning and orienting the tMS device proximate the treatment site, the positioning element including a positioning element controller configured for controlling the automating element so as to effectuate the positioning and the orienting of the tMS device;
 an imaging component, the imaging component including one or more image capturing devices, each image capturing device being configured for capturing one or more images defining a three-dimensional treatment space, the three-dimensional treatment space being occupied by one or more of at least a portion of the peripheral body portion of the subject, the tMS device, and the positioning element, the imaging component being configured for communicating the one or more images defining the three-dimensional space over a network;
 a distance scanner coupled to the housing of the tMS device, the distance scanner being configured for generating and communicating distance data, the distance data including a determination of a distance between the magnetic coil unit and the treatment site on the peripheral body portion of the subject to be treated;
 a control module communicably coupled to the positioning element controller of the positioning element, the magnetic flux controller of the tMS device, the imaging component, and the distance scanner, the control module being configured for:
  receiving the images of the three dimensional space and the distance data,
  employing the images of the three dimensional space and the distance data so as to track movements of one or more of the positioning element and the magnetic coil unit relative to the treatment site during the delivery of the tMS, and
  communicating control instructions to one or more of the positioning element controller and the magnetic flux controller prior to the delivering of transcutaneous magnetic stimulation to the treatment site on the peripheral body portion of the subject; and
 a cloud based server coupled to the control module via the network, the cloud-based server being configured for receiving the images of the three dimensional space and the distance data, processing the images and the distance data to define coordinates of the treatment site within the three-dimensional space, generating the control instructions for moving one or more articulating arm members of the positioning element within the three-dimensional space so as to orientate the magnetic coil unit relative to the treatment site on the peripheral body portion of the subject, transmitting the control instructions to the control module for implementation thereby, and for receiving results data from the control module post implementation of the control instructions after delivering the tMS to the treatment site of the peripheral body portion of the subject.

13. The system in accordance with claim 12, wherein the control instructions include both instructions for moving one or more of the articulating arm members planarly along an X, Y, or Z plane, and rotationally about an X, Y, or Z axis.

14. The system in accordance with claim 13, wherein the control module is further configured for processing the received images of the three dimensional space and the distance data and employing the same to track movements of one or more of the positioning element, the magnetic coil unit, and the treatment site within the three dimensional space.

15. The system in accordance with claim 14, wherein the magnetic coil unit comprises a pressure sensor coupled to the housing of the tMS device, the pressure sensor being configured for sensing a near contact with a portion of the peripheral body portion of the subject, generating proximity data, and signaling for the retracting of one or more of the articulating arm members or the magnetic coil if a proximity limit is threatened to be breached.

16. The system in accordance with claim 15, wherein the tracking is performed real-time so as to maintain an optimal distance between the magnetic coil and the treatment site despite any movements of the subject.

17. The system in accordance with claim 16, wherein the control module is configured for directing the automating element in moving one or more articulating arm members of the positioning element autonomously so as to orientate the magnetic coil unit relative to the treatment site on the peripheral body portion of the subject.

18. The system in accordance with claim 17, wherein the control module is further configured for receiving the proximity data and instructing the positioning element to automatically retract if a proximity limit is threatened to be breached.

19. The system in accordance with claim 18, wherein the results data comprises a subjective evaluation of an amelioration of pain experienced by the subject in response to having received the transcutaneous magnetic stimulation.

20. The system in accordance with claim 19, wherein the cloud based server comprises an artificial intelligence module configured for receiving and corresponding the coordinates of the treatment site within the three-dimensional space with the subject's subjective evaluation of pain experience so as to derive a pattern, the pattern including data pertaining to a correspondence between a result of lessening the pain experienced by implementing a change in the coordinates.

\* \* \* \* \*